(12) United States Patent
Hanna et al.

(10) Patent No.: US 11,344,874 B2
(45) Date of Patent: *May 31, 2022

(54) METHODS FOR REACTING CHEMICAL STREAMS WITH CATALYSTS COMPRISING SILICA, ALUMINA, AND TUNGSTEN

(71) Applicant: Saudi Arabian Oil Company, Dhahran (SA)

(72) Inventors: Brian Hanna, West Roxbury, MA (US); Michele Ostraat, Somerville, MA (US)

(73) Assignee: Saudi Arabian Oil Company, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 17/318,256

(22) Filed: May 12, 2021

(65) Prior Publication Data

US 2021/0260571 A1 Aug. 26, 2021

Related U.S. Application Data

(63) Continuation of application No. 16/256,641, filed on Jan. 24, 2019, now Pat. No. 11,033,892.

(51) Int. Cl.
*B01J 37/00* (2006.01)
*B01J 23/30* (2006.01)
*C07C 5/25* (2006.01)
*C07C 6/02* (2006.01)
(Continued)

(52) U.S. Cl.
CPC .......... *B01J 37/0054* (2013.01); *B01J 23/30* (2013.01); *C07C 5/2512* (2013.01); *C07C 6/02* (2013.01); *C07C 11/06* (2013.01); *C07C 11/08* (2013.01); *B01J 2208/00017* (2013.01);
(Continued)

(58) Field of Classification Search
CPC .................... B01J 37/0054; B01J 23/30; B01J 2208/0001; B01J 2208/00557; B01J 2523/69; B01J 35/002; B01J 35/006; B01J 37/0232; B01J 37/343; B01J 35/008; C07C 5/2512; C07C 6/02; C07C 11/06; C07C 11/08; C07C 2521/14; C07C 2523/30; C07C 4/06; Y02P 20/52
See application file for complete search history.

(56) References Cited

U.S. PATENT DOCUMENTS

| 3,645,684 A | 2/1972 | De Cuir |
| 3,702,886 A | 11/1972 | Argauer et al. |
| 3,865,751 A | 2/1975 | Banks et al. |

(Continued)

FOREIGN PATENT DOCUMENTS

| EP | 276096 A1 | 7/1988 |
| WO | 2005016823 A1 | 2/2005 |

(Continued)

OTHER PUBLICATIONS

U.S. Office Action dated Jul. 9, 2021 pertaining to U.S. Appl. No. 16/909,083, filed Jun. 23, 2020, 35 pages.
(Continued)

*Primary Examiner* — Thuan D Dang
(74) *Attorney, Agent, or Firm* — Dinsmore & Shohl, LLP

(57) ABSTRACT

One or more embodiments presently disclosed is directed to a method for reacting a chemical stream which may include contacting the chemical stream with a catalyst to produce a product stream. The catalyst may include alumina, silica, and a catalytically active compound such as tungsten.

16 Claims, 6 Drawing Sheets

(51) Int. Cl.
  *C07C 11/06* (2006.01)
  *C07C 11/08* (2006.01)
(52) U.S. Cl.
  CPC .. *B01J 2208/00557* (2013.01); *B01J 2523/69* (2013.01); *C07C 2521/14* (2013.01); *C07C 2523/30* (2013.01)

(56) References Cited

U.S. PATENT DOCUMENTS

| | | |
|---|---|---|
| 3,928,177 A | 12/1975 | Hayes |
| 4,507,396 A | 3/1985 | Hickson |
| 4,575,575 A | 3/1986 | Drake et al. |
| 4,684,760 A | 8/1987 | Drake |
| 4,967,013 A | 10/1990 | Steck et al. |
| 5,204,088 A | 4/1993 | Noebel et al. |
| 5,230,789 A | 7/1993 | Chao et al. |
| 5,304,692 A | 4/1994 | Yamada et al. |
| 5,340,560 A | 8/1994 | Rohr et al. |
| 6,099,719 A | 8/2000 | Cody et al. |
| 6,551,567 B2 | 4/2003 | Konya et al. |
| 6,586,785 B2 | 7/2003 | Flagan et al. |
| 6,723,606 B2 | 4/2004 | Flagan et al. |
| 6,780,805 B2 | 8/2004 | Faber et al. |
| 8,097,555 B2 | 1/2012 | Costa et al. |
| 8,246,933 B2 | 8/2012 | Jiang et al. |
| 8,415,267 B2 | 4/2013 | Lee |
| 8,440,874 B2 | 5/2013 | Ramachandran et al. |
| 8,895,795 B2 | 11/2014 | Krawczyk et al. |
| 9,586,198 B2 | 3/2017 | Park et al. |
| 9,682,367 B2 | 6/2017 | Ali et al. |
| 9,969,621 B2 | 5/2018 | Ostraat |
| 2002/0035950 A1 | 3/2002 | Mangold et al. |
| 2002/0177311 A1 | 11/2002 | Schumacher et al. |
| 2004/0101454 A1 | 5/2004 | Johnson et al. |
| 2005/0118096 A1 | 6/2005 | Robson et al. |
| 2008/0011876 A1 | 1/2008 | Ostraat |
| 2010/0056839 A1 | 3/2010 | Ramachandran et al. |
| 2010/0286432 A1 | 11/2010 | Tateno et al. |
| 2010/0286458 A1 | 11/2010 | Iselbom et al. |
| 2011/0077444 A1 | 3/2011 | Butler |
| 2011/0092757 A1 | 4/2011 | Akagishi et al. |
| 2011/0196184 A1 | 8/2011 | Popp et al. |
| 2011/0306691 A1 | 12/2011 | Sosa et al. |
| 2012/0016172 A1 | 1/2012 | Miyazoe et al. |
| 2012/0039782 A1 | 2/2012 | Nicholas |
| 2014/0027346 A1 | 1/2014 | Chaumonnot et al. |
| 2014/0124410 A1 | 5/2014 | Rayo Mayoral et al. |
| 2017/0001925 A1 | 1/2017 | Abudawoud et al. |
| 2017/0136445 A1 | 5/2017 | Ostraat et al. |
| 2017/0320747 A1 | 11/2017 | Ostraat |

FOREIGN PATENT DOCUMENTS

| | | |
|---|---|---|
| WO | 2016061262 A1 | 4/2016 |
| WO | 2016068814 A1 | 5/2016 |
| WO | 2017083162 A1 | 5/2017 |
| WO | 2018136576 A1 | 7/2018 |

OTHER PUBLICATIONS

Spamer, A. et al ("The Reduction of Isomerization Activity on a WO3/SiO2 Metathesis Catalyst," Appl Cata A: General 255 (2003) 153-167) (Year: 2003).
U.S. Office Action dated Jul. 29, 2021 pertaining to U.S. Appl. No. 15/901,442, filed Feb. 21, 2018, 8 pages.
Bhuiyan et al., "Kinetics Modelling of 2-Butene Metathesis over Tungsten Oxide Containing Mesoporous Silica Catalyst", The Canadian Journal of Chemical Engineering, 2014, 92, 1271-1282, Canadian Society for Chemical Engineering.
Bhuiyan et al., "Metathesis of 2-Butene to Propylene over W-Mesoporous Molecular Sieves: A Comparative Study Between Tungsten Containing MCM-41 and SBA-15", Applied Catalysis A: General, 2013, 467, 224-234, Elsevier.
Bukhovko et al., "Continuous Aerosol Flow Reactors for the Controlled Synthesis of heterogeneous Catalyst Particles", AlChE Annual Meeting, Nov. 8-13, 2015.
Debecker et al., "A Non-Hydrolytic Sol-Gel Route to Highly Active MoO2-SiO2-Al2O3 metathesis Catalysts", Catalysis Science & Technology, 2012, 2:6, 1075-1294, RSC Publishing.
Debecker et al., "Aerosol Route to Nanostructured WO3-SiO2-Al2O3 Metathesis Catalysts: Toward Higher Propene Yield", Applied Catalysis A: General, 2014, 470, 458-466, Elsevier.
Debecker et al., "Flame-Made MoO3/SiO2-Al2o3 Metathesis Catalysts with highly Dispersed and Highly Active Molybdate Species", Journal of Catalysis, 2011, 277, 154-163, Elsevier.
Hyeon-Lee et al., "Fractal Analysis of Flame-Synthesized Nanostructured Silica and Titania Powders Using Small-Angle X-Ray Scattering", Langmuir 1998, 5751-5756, 14, American Chemical Society.
International Search Report and Written Opinion for serial No. PCT/US2017/030014, dated Jul. 11, 2017.
International Search Report and Written Opinion pertaining to PCT/US2016/060258 dated Mar. 7, 2017.
Ishihara et al., "Hydrocracking of 1-methylnaphthalene/decahydronaphthalene mixture catalyzed by zeolite-alumina composite supported NiMo catalysts", Fuel Processing Technology 116, pp. 222-227, 2013.
Keskinen et al., "On-Line Characterization of Morphology and Water Adsorption on Fumed Silica Nanoparticles", Aerosol Science and Technology, 2011, 1441-1447, 45, American Association for Aerosol Research.
Lin et al., "Aerosol Processing of Low-Cost Mesoporous Silica Spherical Particles from Photonic Industrial Waste Powder for C02 Capture", Chemical Engineering Journal, 2012, 215-222, 197, Elsevier B.V.
Liu et al., "Alumina with Various pore Structures Prepared by Spray Pyrolysis of Inorganic Aluminum Precursors", I&EC Research, 2013, 52, 13377-13383, ACS Publications.
Lu et al., "Aersol-Assisted Self-Assembly of Mesostructured Spherical Nanoparticles", Nature, 1999, vol. 398, Macmillan Magazines Ltd.
Maksasithorn, Surasa et al., "Preparation of super-microporous WO3-SiO2 olefin metathesis catalysts by the aerosol-assisted sol-gel process", pp. 125-133, Microporous and Mesoporous Materials 213 (2015).
Notice of Allowance pertaining to U.S. Appl. No. 15/146,037, filed May 4, 2016, 8 pages.
Non-Final Office Action dated Sep. 25, 2017 pertaining to U.S. Appl. No. 15/252,733, filed Aug. 31, 2016.
Xie et al., "An Overview of Recent Development in Composite Catalysts from Porous Materials for Various Reactions and Processes", Int. J. Mol. Sci. 11, pp. 2152-2187, 2010.
Notice of Allowance pertaining to U.S. Appl. No. 15/252,733, filed Aug. 31, 2016, 8 pages.
Popoff et al., "Expanding the scope of metathesis: a survey of polyfunctional, single-site supported tungsten systems tor hydrocarbon valorization", Chemical Society Reviews, Issue 23 (2013).
Mazoyer, et al., "Production of propylene from 1-butene on highly active "Bi-functional single active site" catalyst: Tungsten carbene-hydride supported on alumina", http://dialog.proqquest.com/professional/printviewfile?accountid=157282—Accessed: Jul. 6, 2017.
Office Action pertaining to U.S. Appl. No. 15/949,726, dated Jun. 7, 2018.
International Search Report and Written Opinion dated Dec. 3, 2018 pertaining to International Application No. PCT/US2018/046696 filed Aug. 14, 2018.
Senthilkumar et al. "Studies on growth and characterization of heterogeneous tungsten oxide nanostructures for photoelectrochemical and gas sensing applications", Applied Surface Science, vol. 362, pp. 102-108, 2016.
International Search Report and Written Opinion dated May 24, 2019 pertaining to International application No. PCT/US2019/018541 filed Feb. 19, 2019, 17 pgs.
Silverman et al., Methods of Generating Solid Aerosols, J Air Pollution Control Assoc., 6:2 (1956), 76-83.

(56) References Cited

OTHER PUBLICATIONS

Garcia et al. Multifaceted tungsten oxide films grown by thermal evaporation, Surf Coat Tech, 283 (2015) 177-183.
Office Action dated Oct. 3, 2019 pertaining to U.S. Appl. No. 15/998,699, filed Aug. 16, 2018, 32 pgs.
Office Action dated Jan. 24, 2020 pertaining to U.S. Appl. No. 16/256,641, filed Jan. 24, 2019, 7 pgs.
International Search Report and Written Opinion dated Apr. 9, 2020 pertaining to International application No. PCT/US2020/012309 filed Jan. 6, 2020, 12 pgs.
Office Action dated Apr. 1, 2020 pertaining to U.S. Appl. No. 15/998,699, filed Aug. 16, 2018, 16 pgs.
Notice of Allowance and Fee(s) Due dated Jul. 8, 2020 pertaining to U.S. Appl. No. 15/998,699, filed Aug. 16, 2018, 12 pgs.
Office Action dated Mar. 10, 2021 pertaining to U.S. Appl. No. 15/901,442, filed Feb. 21, 2018, 53 pgs.
U.S. Office Action dated Nov. 22, 2021 pertaining to U.S. Appl. No. 15/901,442, filed Feb. 21, 2018, 16 pages.
European Office Action pertaining to application No. 18772960.3 dated May 26, 2021.
U.S. Office Action dated Jan. 10, 2022 pertaining to U.S. Appl. No. 16/909,083, filed Jun. 23, 2020, 26 pages.
Chauvin, J. et al., "Comparative Influence of Surface Tungstate Species and Bulk Amorphous WO3 Particles on the Acidity and Catalytic Activity of Tungsten Oxide Supported on Silica", J. Phys. Chem. C., 2015, 119, pp. 12345-12355.

METHODS FOR REACTING CHEMICAL STREAMS WITH CATALYSTS COMPRISING SILICA, ALUMINA, AND TUNGSTEN

CROSS-REFERENCE TO RELATED APPLICATION

The present application is a continuation of U.S. application Ser. No. 16/256,641, filed Jan. 24, 2019, and entitled "Methods for Reacting Chemical Streams with Catalysts Comprising Silica, Alumina, and Tungsten," the entire contents of which are incorporated by reference in the present disclosure.

TECHNICAL FIELD

Embodiments of the present disclosure generally relate to chemical processing and, more specifically, to catalyzed chemical processing.

BACKGROUND

In recent years, there has been a dramatic increase in the demand for propene to feed the growing markets for polypropylene, propylene oxide, and acrylic acid. Currently, most of the propene produced worldwide is a by-product from steam cracking units (57%), which primarily produce ethylene, or a by-product from Fluid Catalytic Cracking (FCC) units (30%), which primarily produce gasoline. These processes cannot respond adequately to a rapid increase in propene demand.

Raffinate is the residue C4 stream from a naphtha cracking process or from a gas cracking process when components are removed (the C4 stream typically containing, as its chief components, n-butane, 1-butene, 2-butene, isobutene and 1,3-butadiene, and optionally some isobutane and said chief components together forming up to 99% or more of the C4 stream). Specifically, Raffinate-2 is the C4 residual obtained after separation of 1,3-butadiene and isobutene from the C4 raffinate stream and consists mainly of cis- or trans-2-butene, 1-butene, and n-butane. Similarly, Raffinate-3 is the C4 residual obtained after separation of 1,3-butadiene, isobutene, and 1-butene from the C4 raffinate stream and consists mainly of cis- or trans-2-butene, n-butane, and unseparated 1-butene. Utilizing Raffinate-2 and Raffinate-3 streams for conversion to propene is desirable to increase the available supply of propene.

Development of metathesis catalysts to convert Raffinate-2 and Raffinate-3 streams to propene have relied on wet impregnation to impregnate a metal oxide into a previously synthesized support material or on including a metal oxide into a premixture that is formed into the catalyst support material. However, wet impregnation or including the metal oxide into the catalyst premix are limited in that a large proportion of the metal oxide is bound in the interior portions of the catalyst support material and likely less accessible to reactants of the metathesis reaction. Additionally, control of the properties of the resulting metathesis catalyst is limited.

SUMMARY

Ongoing needs exist for catalysts and associated chemical processing methods which incorporate such catalysts which may be utilized to isomerize, metathesize, or both, chemical streams that include alkenes. Catalysts which may be suitable for such reactions include those comprising silica and tungsten. As is presently described, it has been discovered that the incorporation of particular amounts of alumina (for example, 0.1 weight percent to 5 weight percent) into the catalyst may improve catalytic functionality at one or more reaction conditions. In one or more embodiments, the catalyst may include a catalyst support particle which includes silica and alumina, and a catalytically active compound deposited onto a surface of the catalyst support particle, and may include from 0.1 weight percent to 5 weight percent alumina. It has been found that such catalysts may have greater catalytic activity at relatively low reaction temperatures (such as less than or equal to 500° C.) than similar catalysts which contain other amounts of alumina (or those lacking any alumina). In one or more additional embodiments, the catalyst may include silica, alumina, and tungsten in a mixed form, where the weight ratio of alumina to silica is from 0.01:99.9 to 5:95. Such a catalyst may have greater catalytic activity at temperatures of 500° C. or less than similar catalysts with greater amounts of tungsten but contain other ratios of alumina to silica (or those lacking any alumina). Such catalysts may be formed by aerosol processing techniques, which are described in detail in the present disclosure.

According to one or more embodiments, a method for reacting a chemical stream may comprise contacting the chemical stream with a catalyst to produce a product stream. The chemical stream may comprise one or more alkenes and the product stream comprises one or more alkenes which are the result of isomerization, metathesis, or both, of the one or more alkenes of the chemical stream. The contacting of the chemical stream with the catalyst may be at a temperature of less than or equal to 500° C. The catalyst may comprise a plurality of catalyst support particles comprising from 0.1 weight percent to 5 weight percent alumina and from 95 weight percent to 99.9 weight percent of silica based on the total weight of the catalyst support particles, and a catalytically active compound deposited onto surfaces of the plurality of catalyst support particles, the surfaces of the plurality of catalyst support particles being accessible to gases and vapors. The catalytically active compound may comprise tungsten and the catalytically active compound may be deposited on from 1% to 50% of the surfaces of the catalyst support particles that are accessible to gases and vapors.

According to one or more additional embodiments, a method for reacting a chemical stream may comprise contacting the chemical stream with a catalyst to produce a product stream. The chemical stream may comprise one or more alkenes and the product stream may comprise one or more alkenes which are the result of isomerization, metathesis, or both, of the one or more alkenes of the chemical stream. The contacting of the chemical stream with the catalyst may be at a temperature of less than 550° C. The catalyst may be produced by a method comprising generating an aerosolized flow of catalyst support particles, wherein the catalyst support particles comprise from 0.1 weight percent to 5 weight percent alumina and from 95 weight percent to 99.9 weight percent silica based on the total weight of the catalyst support particles, heating a catalytically active compound precursor comprising tungsten to produce a catalytically active compound precursor vapor, contacting the aerosolized flow of catalyst support particles with the catalytically active compound precursor vapor, and condensing the catalytically active compound precursor to produce the catalyst comprising a catalytically active compound deposited on surfaces of the catalyst support particles.

According to one or more yet additional embodiments, a method for reacting a chemical stream may comprise contacting the chemical stream with a catalyst to produce a product stream. The chemical stream may comprise one or more alkenes and the product stream comprises one or more alkenes which are the result of isomerization, metathesis, or both, of the one or more alkenes of the chemical stream. The contacting of the chemical stream with the catalyst may be at a temperature of less than or equal to 500° C. The catalyst may be produced by a process comprising forming a catalyst precursor mixture comprising a diluent and a catalyst precursor, the catalyst precursor comprising a tungsten precursor, an alumina precursor, and a silica precursor, aerosolizing the catalyst precursor mixture, drying the aerosolized catalyst precursor mixture to form a dried catalyst precursor, and reacting the dried catalyst precursor to yield the catalyst, the catalyst comprising a silica or silica and alumina support comprising tungsten distributed within the silica and alumina support, and wherein the weight ratio of alumina to silica is from 0.1:99.9 to 5:95.

Additional features and advantages of the described embodiments will be set forth in the detailed description which follows, and in part will be readily apparent to those skilled in the art from that description or recognized by practicing the described embodiments, including the detailed description which follows, the claims, as well as the appended drawings.

BRIEF DESCRIPTION OF THE DRAWINGS

The following detailed description of specific embodiments of the present disclosure can be best understood when read in conjunction with the following drawings, where like structure is indicated with like reference numerals and in which.

Figure 1:
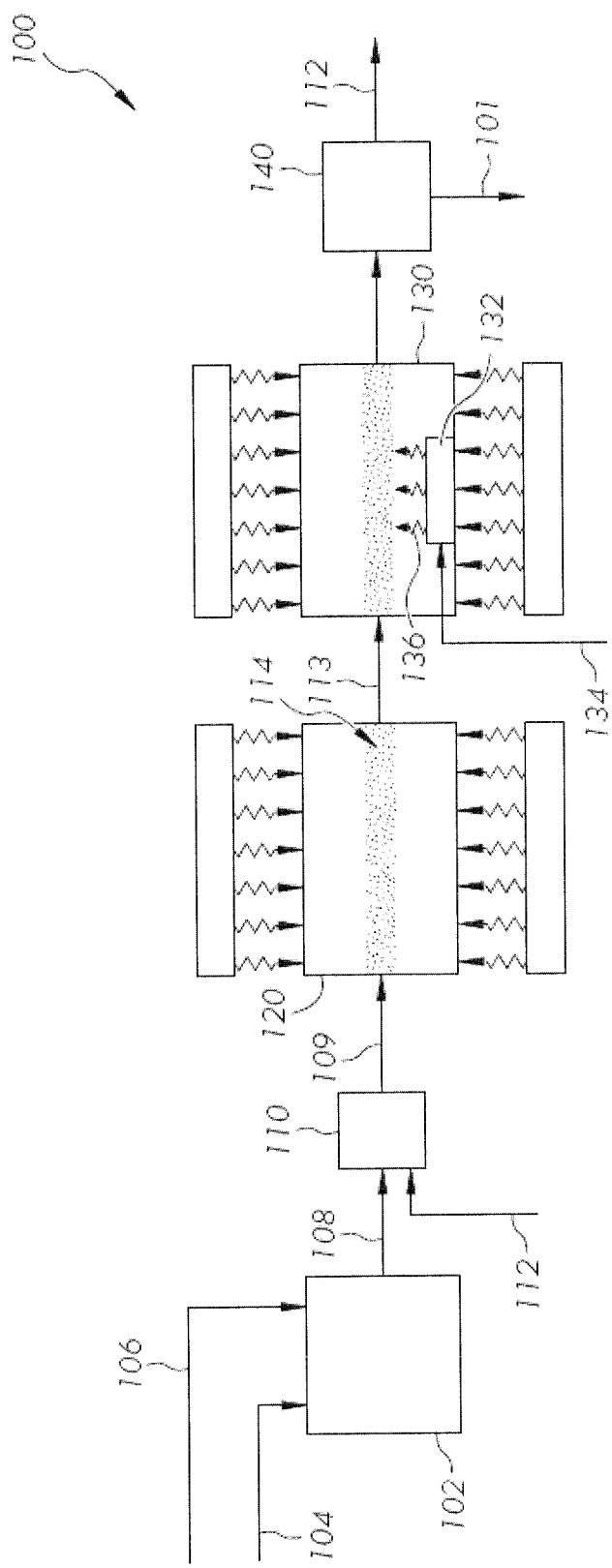
FIG. 1 schematically depicts an aerosol processing system, in accordance with one or more embodiments of the present disclosure.

For the purpose of describing the simplified schematic illustrations and descriptions of the several figures, the numerous valves, temperature sensors, electronic controllers, and the like that may be employed and well known to those of ordinary skill in the art of certain chemical processing operations are not included. Further, accompanying components that are often included in typical chemical processing operations, carrier gas supply systems, pumps, compressors, furnaces, or other subsystems are not depicted. It should be understood that these components are within the spirit and scope of the present embodiments disclosed. However, operational components, such as those described in the present disclosure, may be added to the embodiments described in this disclosure.

Arrows in the drawings may refer to process streams. However, the arrows may equivalently refer to transfer lines which may serve to transfer process streams between two or more system components. Additionally, arrows that connect to system components may define inlets or outlets in each given system component. The arrow direction corresponds generally with the major direction of movement of the materials of the stream contained within the physical transfer line signified by the arrow. Furthermore, arrows which do not connect two or more system components may signify a product stream which exits the depicted system or a system inlet stream which enters the depicted system. Product streams may be further processed in accompanying chemical processing systems or may be commercialized as end products.

Additionally, arrows in the drawings may schematically depict process steps of transporting a stream from one system component to another system component. For example, an arrow from one system component pointing to another system component may represent "passing" a system component effluent to another system component, which may include the contents of a process stream "exiting" or being "removed" from one system component and "introducing" the contents of that product stream to another system component.

It should be understood that two or more process streams are "mixed" or "combined" when two or more lines intersect in the schematic flow diagrams of the figures. Mixing or combining may also include mixing by directly introducing both streams into a like system component, such as a vessel, aerosolizer, heating zone, furnace, or other system component. For example, it should be understood that when two streams are depicted as being combined directly prior to entering a system component, the streams could equivalently be introduced into the system component and be mixed in the system component.

Reference will now be made in greater detail to various embodiments, some embodiments of which are illustrated in the accompanying drawings. Whenever possible, the same reference numerals will be used throughout the drawings to refer to the same or similar parts.

DETAILED DESCRIPTION

Embodiments of the present disclosure are directed to methods for reacting chemical streams, sometimes referred to as feed streams, which utilize particular catalysts which are presently described. The catalyst may metathesize, isomerize, or both, contents of the chemical stream. In one or more embodiments, the chemical streams that are reacted may include alkenes such as, for example, various C2, C3, C4, or C5 alkenes. Contact between the chemical stream and the catalyst may produce a product stream. Each of the feed stream and the product stream may include alkenes. In one or more embodiments, the chemical stream may comprise at least 5 mol. % of n-butene, such as 2-butene. The product stream may comprise at least 10 mol. % of propylene. The catalytic activity (that is, the metathesis reaction rate, isomerization reaction rate, or both, of one or more alkenes) may be increased by use of particular amounts of alumina. In one or more embodiments, the input chemical stream may include a composition identical or similar to that shown in Table 1. In additional embodiments, a feed stream may include ranges of the components listed in Table 1 plus or minus 1 wt. %, 2 wt. %, 3 wt. %, 4 wt. %, or 5 wt. %. The composition of Table 1 may be an example Raffinate 2 stream.

TABLE 1

| Chemical Composition | Weight percent in feed stream |
| --- | --- |
| Lights (lighter than other chemicals listed in Table 1) | 1.79% |
| n-Butane | 10.71% |
| Isobutane | 3.57% |
| Butene-1 | 46.4% |
| Trans-butene-2 | 21.4% |
| Cis-butene-2 | 16.07% |
| 1,3-Butadiene | Trace (less than 0.5%) |

It should be appreciated that at least two distinct embodiments of catalysts are contemplated herein: (1) a catalyst where tungsten is deposited onto the surface of the catalytic particles, and (2) a catalyst where the tungsten is dispersed throughout the catalytic particles. In each embodiment, it has been observed that a particular amount of alumina in the catalyst enhances catalytic functionality under certain reaction conditions and that the presence of even small amounts of alumina to enhance the performance of the catalyst may be desirable. The methods for reacting chemical streams utilizing these catalysts are described in detail presently. It should be understood that each embodiment type may be suitable with reduced catalytic loading (for example, tungsten loading of less than 5 weight percent, such as approximately 2.5 weight percent) and at relatively low reaction temperatures (for example, less than 500° C.) and/or relatively high feed flowrates (for example, a space velocity of greater than 1000/hour).

Surface Deposited Tungsten Embodiments

In one or more embodiments, catalysts and methods of producing catalysts via aerosol processing to deposit a catalytically active compound onto the surfaces of catalyst support particles accessible to gases and vapors are disclosed. In embodiments, a method of forming a catalyst comprises generating an aerosolized flow of catalyst support particles, vaporizing a catalytically active compound precursor to produce a catalytically active compound precursor vapor, contacting the aerosolized flow of catalyst support particles with the catalytically active compound precursor vapor, and condensing the catalytically active compound precursor vapor to produce the catalyst comprising the catalytically active compound deposited on surfaces of the catalyst support particles. The catalyst support particles may include from 0.1 weight percent to 5 weight percent alumina based on the total weight of the catalyst support particles.

In one or more embodiments, catalysts with surface deposited tungsten, such as applied through an evaporation technique, which include 0.1 weight percent to 5 weight percent alumina in their catalyst support particles may have greater catalytic activity at relatively low temperatures, such as at or below 500° C., at or below 475° C., or even at or below 450° C. It was observed that similar catalysts which lacked 0.1 to 5 weight percent alumina had reduced catalytic activity at these lower reaction temperatures. The presently disclosed catalysts may also have superior catalytic activity at greater feed flow rates, such as space hour velocities of greater than 1000/hour, 1500/hour, 2000/hour, 2500/hour, 3000/hour, or even 3500/hour. In some embodiments, yields may be greatest at from 800/hour to 1000/hour, such as about 900/hour.

The methods of producing catalysts according to one or more embodiments described in this disclosure allow for continuous production of catalysts that may have a catalytically active compound deposited onto the surfaces of catalyst support particles. By depositing the catalytically active compound onto the surfaces of catalyst support particles that are accessible to gases and vapors, the catalytically active compound may be accessible to reactants rather than being buried or partially-buried in the interior of the catalyst support material. If the catalytically active compound is buried or partially-buried in the interior of the catalyst support material, the catalytically active compound may be inaccessible to the reactants.

The catalytically active compound deposited on the surface of the catalyst support particles by the aerosol processing methods described in this disclosure are highly active. The catalysts formed by the disclosed methods provide performance equivalent to state-of-the-art catalysts having higher loading of the catalytically active compound. In some examples, the catalysts synthesized by the aerosol processing methods described in this disclosure have an amount of catalytically active compound less than 50%, or even less than 25% of the catalytically active compound of other prepared catalysts. The catalysts synthesized by the aerosol processing methods of this disclosure provide catalytic activity that is equivalent to or superior to the catalytic activity performance of other prepared catalysts.

As used in this disclosure, a "catalyst" refers to a solid particulate comprising catalyst support particles and at least one catalytically active compound.

As used in this disclosure, a "catalytically active compound" refers to any substance that increases the rate of a specific chemical reaction. Catalysts described in this disclosure may be utilized to promote various reactions, such as, but not limited to, isomerization, metathesis, cracking, hydrogenation, demetallization, desulfurization, denitrogenation, other reactions, or combinations of these. The catalytically active compound may be a metal, metal oxide, other catalytically active compound, or combinations of these. In some embodiments, the catalytically active compound may be a metal, such as platinum, gold, palladium, rhodium, iridium, chromium, other metal, or combinations of these. Alternatively, the catalytically active compound may include a metal oxide, such as one or more than one oxide of a metal from Groups 6-10 of the IUPAC Periodic Table. In some embodiments, the metal oxide may include at least one oxide of molybdenum, rhenium, tungsten, manganese, titanium, cerium or any combination of these. In some embodiments, the metal oxide may be tungsten oxide. The morphology, type, and amount of the catalytically active compound deposited on the surface of the catalyst support may determine the catalytic activity of the catalyst. The following methods and systems are described in the context of synthesizing isomerization catalysts, metathesis catalysts, or metathesis and isomerization catalysts having a metal oxide as the catalytically active compound deposited on the surface of a catalyst support particle. However, it is understood that the methods and system may be utilized to synthesize other types of catalysts.

Embodiments of the catalysts synthesized by the disclosed aerosol processing systems and methods generally comprise catalyst support particles having a catalytically active compound deposited on the surfaces of the catalyst support particles. The catalyst support particles may include a combination of silica and alumina. The catalyst support particles may include from 0.1 weight percent to 5 weight percent alumnia based on the total weight of the catalyst support particles.

Embodiments of a method of producing the catalyst having the catalytically active compound deposited on the surface of the catalyst support particles will now be described. In some embodiments, the method may include generating an aerosolized flow of catalyst support particles, heating a catalytically active precursor to produce a catalytically active compound precursor vapor, contacting the aerosolized flow of catalyst support particles with the catalytically active compound precursor vapor, and condensing the catalytically active compound precursor vapor to produce the catalyst comprising the catalytically active compound deposited on the surface of the catalyst support particles.

In some embodiments, the catalytically active compound precursor vapor may condense directly onto the surface of the catalyst support particles. Directly depositing the catalytically active compound precursor vapor onto the surface of the catalyst support particles may include heterogeneous nucleation of the catalytically active compound precursor vapor on the surfaces of the catalyst support particles. Additionally, in some embodiments, the catalytically active compound may condense onto catalytically active compound previously deposited on the catalyst support particle, which may grow the additionally deposited catalytically active compound into small clusters or particles on the surface of the catalyst support particles if the vapor preferentially deposits onto (or migrates to) the previously deposited catalytically active material. Alternatively, in some embodiments, the catalytically active compound precursor vapor may condense onto itself (homogeneous nucleation) to create clusters or particles of the catalytically active compound, which may then diffuse to the catalyst support particles and deposit onto the surface of the catalyst support particles.

In some embodiments, the aerosolized flow of catalyst support particles may be generated by aerosolizing a catalyst support precursor mixture and drying, reacting, or drying and reacting the aerosolized catalyst support precursor mixture to form the catalyst support particles. The aerosol processing method may be a continuous process to continuously produce the catalyst from the catalyst support precursor and the catalytically active compound precursor.

Referring to FIG. 1, an aerosol processing system 100 for synthesizing the catalyst 101 comprising a catalytically active compound deposited on the surfaces of a catalyst support is depicted. As shown in FIG. 1, the aerosol processing system 100 may include a vessel 102 for mixing at least a catalyst support precursor 104 and a diluent 106 to form a catalyst support precursor mixture 108. The aerosol processing system 100 may include an aerosolizing unit 110, a first heating zone 120 downstream of the aerosolizing unit 110, and a second heating zone 130 downstream of the first heating zone 120. The catalyst support precursor mixture 108 may be passed to the aerosolizing unit 110. The aerosolizing unit 110 may aerosolize the catalyst support precursor mixture 108 into a plurality of droplets of the catalyst support precursor mixture, referred to in this disclosure as the aerosolized catalyst support precursor mixture 109. A carrier gas 112 may be introduced to the aerosolizing unit 110 to convey the aerosolized catalyst support precursor mixture 109 out of the aerosolizing unit 110 and through the first heating zone 120, in which the droplets of the aerosolized catalyst support precursor mixture 109 may be dried, reacted, or both to form a plurality of solid catalyst support particles 114 aerosolized in an aerosol 113 comprising the carrier gas 112 and the catalyst support particles 114.

The aerosol 113 comprising the carrier gas 112 and the catalyst support particles 114 may pass into and through the second heating zone 130. The second heating zone 130 may include a source 132 of a catalytically active compound precursor 134. Heat from the second heating zone 130 may cause the catalytically active compound precursor 134 in the source 132 to vaporize to form a catalytically active compound precursor vapor 136. The catalytically active compound precursor vapor 136 may contact the plurality of catalyst support particles 114 in the aerosol 113 and may condense on the surfaces of the catalyst support particles 114 to form the catalyst 101. Once condensed onto the catalyst support particles 114, the catalytically active compound may undergo surface diffusion, in which the atoms, molecules, or both of the catalytically active compound may migrate on the surface of the catalyst support particles 114 until the atoms, molecules, or both reach a favorable energy state. In some embodiments, the catalytically active compound precursor vapor 136 may homogeneously nucleate to form catalytically active compound clusters or particles that may contact the plurality of catalyst support particles 114 and deposit on the surfaces of the catalyst support particles 114 to form the catalyst 101. In some embodiments, the catalytically active compound clusters or particles may have a particle size of up to 20 nanometers (nm). In some embodiments, the aerosol processing system 100 may include a separator 140 for separating the catalyst 101 from the carrier gas 112 and collecting the catalyst 101.

The catalyst support precursor 104 may include a silica precursor, an alumina precursor, or combinations of these. Examples of the silica precursor in the catalyst support precursor 104 may include, but are not limited to, fumed silica, colloidal silica, silane ($SiH_4$), silicon tetrachloride, tetraethyl orthosilicate (TEOS), or combinations of these. In some embodiments, the silica precursor may include fumed silica. In embodiments, the catalyst support precursor 104 may include a plurality of precursor materials, such as a combination of silica precursors and alumina precursors for example. In some embodiments, the catalyst support precursor 104 may comprise from 95 weight percent (weight percent) to 99.9 weight percent silica precursor, based on the total weight of the catalyst support precursor 104 prior to combining the catalyst support precursor 104 with the diluent 106 to make the catalyst support precursor mixture 108. In embodiments, the catalyst support precursor 104 may include from 95 weight percent to 96 weight percent, 96 weight percent to 97 weight percent, from 97 weight percent to 98 weight percent, from 98 weight percent to 99 weight percent, from 99 weight percent to 99.9 weight percent, or a combination thereof, of silica precursor, based on the total weight of the catalyst support precursor 104 prior to combining the catalyst support precursor 104 with the diluent 106 to make the catalyst support precursor mixture 108.

Examples of alumina precursors may include, but are not limited to, aluminum nitrate ($Al(NO_3)_3$), fumed alumina, aluminum salts such as $AlCl_3$, $AlPO_4$, or $Al_2(SO_4)_3$ and their hydrates, other alumina precursors, or combinations of these. In some embodiments, the alumina precursor may comprise aluminum nitrate ($Al(NO_3)_3$). In some embodiments, the catalyst support precursor 104 may include from 0.1 weight percent to 5 weight percent alumina precursor, based on the total weight of the catalyst support precursor 104 prior to combining the catalyst support precursor 104 with the diluent 106 to make the catalyst support precursor mixture 108. In other examples, the catalyst support precursor 104 may include from 0.1 weight percent to 1 weight percent, from 1 weight percent to 2 weight percent, from 2 weight percent to 3 weight percent, from 3 weight percent to 4 weight percent, from 4 weight percent to 5 weight percent, or combinations thereof, of alumina precursor, based on the total weight of the catalyst support precursor 104 prior to combining the catalyst support precursor 104 with the diluent 106 to make the catalyst support precursor mixture 108.

In some embodiments, the catalyst support precursor mixture 108 may optionally include one or a plurality of dopants. The catalyst support precursor mixture 108 may include a dopant to modify one or more than one characteristic or property of the catalyst support particles 114 formed from the catalyst support precursor mixture 108. Examples of dopants may include, but are not limited to, titania, rhenia, phosphates, or combinations of these. Additionally, dopants may include inert constituents, sacrificial constituents, or both, in the catalyst support precursor mixture 108. Non-limiting examples of inert and sacrificial constituents may include polystyrene latex, other polymers, or combinations of polymers. When heated to high temperatures, the polystyrene latex burns off, leaving pores where the polystyrene latex was previously. These inert and sacrificial constituents may be used to modify the surface area of the catalyst support particles 114. Synthesis of the catalyst 101 via aerosol processing allows for the inclusion of dopants during initial synthesis of the catalyst support particles 114 as compared to applying one or a plurality of dopant compounds to the catalyst 101 using a post-synthesis addition process, such as a coating process for example. In embodiments, one or more than one dopant may be included in the catalyst support precursor mixture 108 such that the dopant(s) are thus included in and distributed throughout the catalyst support particles 114 during the aerosol processing.

The diluent 106 may be water, an organic solvent, or a combination of water and at least one organic solvent. Example organic solvents may include methanol, ethanol, acetone, or a combination of solvents. In some embodiments, the diluent 106 may be water such that the catalyst support precursor mixture 108 is an aqueous catalyst support precursor mixture. In other embodiments, the diluent 106 may include a combination of water and at least one organic solvent.

In some embodiments, the catalyst support precursor mixture 108 may be absent a surfactant. Inclusion of a surfactant in the catalyst support precursor mixture 108 may require an additional calcination step to prepare the catalyst 101. In some cases, the presence of a surfactant in the catalyst support precursor mixture 108 may result in an undesired residue on the catalyst 101 which may degrade the performance of the catalyst 101 and/or be toxic or hazardous to health.

The catalyst support precursor mixture 108 may be formed as a solution, a suspension, or both of the catalyst support precursor 104 in the diluent 106. For example, with fumed catalyst support precursors, such as fumed silica precursors or fumed alumina precursors, or colloidal precursors, a suspension is formed for the catalyst support precursor mixture 108. Alternatively, for a catalyst support precursor 104 comprising metal salts, the catalyst support precursor mixture 108 may be a solution of the catalyst support precursor 104 in the diluent 106. In some embodiments, the catalyst support precursor 104 may include fumed silica precursor or fumed alumina precursor and a metal salt such that the catalyst support precursor mixture 108 comprises a suspension of the fumed components in a solution comprising the metal salt dissolved in the diluent 106.

The catalyst support precursor mixture 108 may have an amount of the catalyst support precursor 104 sufficient so that the diluent is removed to form the solid catalyst support particles 114 from the droplets of the catalyst support precursor mixture 108 during the residence time in the first heating zone 120. In embodiments, the catalyst support precursor mixture 108 may have from 1 weight percent to 20 weight percent catalyst support precursor 104, based on the total weight of the catalyst support precursor mixture 108. In other embodiments, the catalyst support precursor mixture 108 may comprise from 1 weight percent to 16 weight percent, from 1 weight percent to 12 weight percent, from 1 weight percent to 8 weight percent, from 1 weight percent to 4 weight percent, from 4 weight percent to 20 weight percent, from 4 weight percent to 16 weight percent, from 4 weight percent to 12 weight percent, from 4 weight percent to 8 weight percent, from 8 weight percent to 20 weight percent, from 8 weight percent to 16 weight percent, from 8 weight percent to 12 weight percent, from 12 weight percent to 20 weight percent, from 12 weight percent to 16 weight percent, or from 16 weight percent to 20 weight percent catalyst support precursor 104, based on the total weight of the catalyst support precursor mixture 108. In some embodiments, one or a plurality of dopants may be mixed with the catalyst support precursor mixture 108 prior to aerosolizing the catalyst support precursor mixture 108.

In some embodiments, once formed, the solid catalyst support particles may have from 0.1 weight percent to 5 weight percent alumnia based on the total weight of the catalyst support particles 114. In other embodiments, the catalyst support precursor mixture 108 may comprise from 0.1 weight percent to 1 weight percent, from 1 weight percent to 2 weight percent, from 2 weight percent to 3 weight percent, from 3 weight percent to 4 weight percent, from 4 weight percent to 5 weight percent, or combinations thereof, of alumnia based on the total weight of the catalyst support particles 114.

The catalyst support precursor mixture 108 may be aerosolized to form an aerosolized catalyst support precursor mixture 109, which comprises a plurality of droplets of the catalyst support precursor mixture 108 dispersed in the carrier gas 112. As shown in FIG. 1, the catalyst support precursor mixture 108 may be aerosolized in the aerosolizing unit 110 to form the aerosolized catalyst support precursor mixture 109. A variety of aerosolizing units 110 are envisioned, as long as they generate a liquid spray of droplets. Examples of aerosolizing units 110 may include, but are not limited to, ultrasonic transducers, spray nozzles, other aerosolizing devices, or combinations of these. In some embodiments, an ultrasonic transducer may be used to generate the aerosolized catalyst support precursor mixture 109. Ultrasonic transducers may be readily scalable and highly controllable.

The type of aerosolizing unit 110 and the specifications of the aerosolizing unit 110 may influence the particle size of the catalyst support particles 114 by influencing the average droplet size of the aerosolized catalyst support precursor mixture 109. For example, an aerosolizing unit 110 configured to produce smaller sized droplets will generally result in smaller catalyst support particles 114 produced by the aerosol processing method. The type, specifications, or both of the aerosolizing unit 110 may also influence the particle size of the catalyst support particles 114 by increasing the turbulence of the aerosolized catalyst support precursor mixture 109, which may cause some droplets to collide and combine into larger droplets. In some embodiments, the aerosolizing unit 110 may be capable of producing droplets of the catalyst support precursor mixture 108 having droplet sizes from 0.1 µm to 100 µm, from 0.1 µm to 20 µm, from 0.5 µm to 100 µm, or from 0.5 µm to 20 µm.

As previously discussed, a carrier gas 112 is introduced to the aerosolizing unit 110. The aerosolized catalyst support precursor mixture 109 is aerosolized in the carrier gas 112, which then transports the droplets of the aerosolized catalyst support precursor mixture 109 through the heating zones, such as the first heating zone 120 and the second heating zone 130. In some embodiments, the carrier gas 112 is air. Alternatively, in other embodiments, the carrier gas 112 may include at least one of nitrogen, argon, helium, or combinations of these gases. In yet further embodiments, the carrier gas 112 may include a mixture that contains a reactant or dopant for the formation of the catalyst support particles 114. For example, the carrier gas 112 may include silane ($SiH_4$). The selection of a non-reactive gas or a reactive gas or a combination of both for the carrier gas 112 depends on the catalyst support precursors 104 utilized and the desired properties of the catalyst 101.

In some embodiments, the method of synthesizing the catalyst may include aerosolizing a dopant stream concurrently with aerosolizing the catalyst support precursor mixture 108 to form an aerosol comprising the aerosolized catalyst support precursor mixture 109 and the aerosolized dopant.

Referring to FIG. 1, the aerosolized catalyst support precursor mixture 109 is passed to and through at least a first heating zone 120 and a second heating zone 130 downstream of the first heating zone 120 to form the catalyst 101. The method of synthesizing the catalyst 101 includes drying the aerosolized catalyst support precursor mixture 109, reacting the aerosolized catalyst support precursor mixture 109, or both in the first heating zone 120 to form a plurality of catalyst support particles 114. The droplets of aerosolized catalyst support precursor mixture 109 are passed to the first heating zone 120, in which heat from the first heating zone 120 dries the droplets of the aerosolized catalyst support precursor mixture 109 to form the plurality of catalyst support particle 114. In some embodiments, the first heating zone 120 may be a region of a first furnace, and the carrier gas 112 may convey the droplets of the aerosolized catalyst support precursor mixture 109 through the region of the first furnace. Alternatively, the first heating zone 120 may comprise a first section of a reaction tube disposed within the first furnace, and the carrier gas 112 may convey the droplets of the aerosolized catalyst support precursor mixture 109 through the reaction tube. In these embodiments having the reaction tube, the heat from the furnace may be transferred to the reaction tube, conducted through the wall of the reaction tube, and then transferred to the droplets of the aerosolized catalyst support precursor mixture 109 flowing through the reaction tube.

In addition to drying the droplets of the aerosolized catalyst support precursor mixture 109, the first heating zone 120 may initiate formation of crystallinity within the catalyst support particles 114 formed from drying the droplets of aerosolized catalyst support precursor mixture 109. It is noted that the aerosolized catalyst support precursor mixture 109 need not be fully dried prior to initiation of crystallization. As the aerosolized catalyst support precursor mixture 109 passes through the first heating zone 120, the droplets of the aerosolized catalyst support precursor mixture 109 begin to dry and the catalyst support precursor 104 becomes more concentrated in each of the droplets. Subsequently, as the droplets are heated further, the dried or partially dried catalyst support precursor 104 can react to form amorphous structures, crystalline structures, or a combination of amorphous and crystalline structures depending upon the catalyst support precursor chemistry.

In alternative embodiments, one or more reactive gases may be introduced to the first heating zone 120 and may decompose at high temperatures in the first heating zone 120, react in the first heating zone 120, and nucleate to form the plurality of catalyst support particles 114. For example, a reactive gas, such as but not limited to $SiH_4$, may be introduced to the first heating zone 120. The $SiH_4$ may thermally decompose in the first heating zone 120 to produce silicon atoms (Si) and hydrogen molecules ($H_2$). In the presence of oxygen ($O_2$) in the first heating zone 120, the silicon (Si) may react with the oxygen gas ($O_2$) to produce $SiO_2$. This $SiO_2$ may nucleate in the first heating zone 120 to produce $SiO_2$ particles. The $SiO_2$ particles may grow in size through continued decomposition of $SiH_2$, reaction of Si with $O_2$ to produce $SiO_2$, and condensation of $SiO_2$ onto the $SiO_2$ particles to produce the plurality of catalyst support particles 114.

In still other embodiments, the reactive gas may be introduced to the first heating zone 120 and may decompose in the first heating zone 120 to deposit a secondary material onto the surfaces of the catalyst support particles 114. For example, $SiH_4$ may be introduced to the first heating zone 120, may decompose into Si and $H_2$, and react with $O_2$ to form $SiO_2$. In these examples, the $SiO_2$ may condense on the outer surfaces of the catalyst support particles 114 formed from the aerosolized catalyst support precursor mixture 109. In some embodiments, the $SiO_2$ formed from decomposition of $SiH_4$ may condense onto the droplets of aerosolized catalyst support precursor mixture 109 in the first heating zone 120 to include the $SiO_2$ into the catalyst support particles 114. Although described in the context of $SiH_4$, other reactive gases are contemplated.

In embodiments, the first heating zone 120 may be maintained at a temperature sufficient to evaporate, react, or decompose the diluent 106 from the droplets of the aerosolized catalyst support precursor mixture 109 to form a plurality of solid catalyst support particles 114. In embodiments, the first heating zone 120 may be maintained at a first temperature of from 100° C. to 1500° C. In other embodiments, the first heating zone may be maintained at a temperature of from 200° C. to 1450° C., from 200° C. to 1400° C., from 200° C. to 1300° C., from 500° C. to 1500° C., 500° C. to 1450° C., from 500° C. to 1400° C., from 500° C. to 1300° C., from 600° C. to 1500° C., 600° C. to 1450° C., from 600° C. to 1400° C., from 600° C. to 1300° C., from 1000° C. to 1500° C., 1000° C. to 1450° C., from 1000° C. to 1400° C., from 1000° C. to 1300° C., from 1300° C. to 1500° C., 1300° C. to 1450° C., from 1300° C. to 1400° C., or from 1400° C. to 1500° C. In further embodiments, to merely dry the droplets of the aerosolized catalyst support precursor mixture 109, the first heating zone 120 may be heated to a temperature from 100° C. to 800° C. If the temperature in the first heating zone 120 is too great, the droplets of the aerosolized catalyst support precursor mixture 109 may rapidly dry to form a shell structure of the catalyst support precursor 104 rather than solid catalyst support particles 114. Catalyst support shells are less able to withstand the stress and pressures exerted on the catalyst 101 during downstream processing, use, or both compared to the solid catalyst support particles 114.

In some embodiments, the first heating zone 120 may comprise a plurality of temperature zones. Each of the temperature zones may operate at a different temperature. For example, a first temperature zone operated at a temperature of from 100° C. to 800° C. may be utilized to at least partially dry or fully dry the droplets of the aerosolized catalyst support precursor mixture 109, and a second temperature zone operated at a temperature of from 800° C. to 1500° C. may be utilized to react the catalyst support precursors 104, crystallize the catalyst support precursors 104, or both to form the catalyst support particles 114. In embodiments, the first heating zone 120 may be operated at ambient pressure. In other embodiments, the first heating zone 120 may be operated at atmospheric pressure.

The residence time of the aerosolized catalyst support precursor mixture 109 in the first heating zone 120 may be sufficient to produce fully dried and reacted catalyst support particles 114. In some embodiments, the residence time of the aerosolized catalyst support precursor mixture 109 in the first heating zone 120 may be from 0.1 seconds to 9 seconds. In other embodiments, the residence time of the aerosolized catalyst support precursor mixture 109 in the first heating zone 120 may be from 0.1 seconds to 8 seconds, 0.1 second to 6 seconds, from 0.1 second to 4 seconds, from 0.5 second to 9 seconds, from 0.5 seconds to 8 seconds, from 0.5 seconds to 6 seconds, from 0.5 second to 4 seconds, from 1 second to 9 seconds, from 1 second to 8 seconds, from 1 second to 6 seconds, from 1 second to 4 seconds, from 2 seconds to 9 seconds, from 2 seconds to 8 seconds, from 2 seconds to 6 seconds, or from 2 seconds to 4 seconds. If the residence time is of insufficient duration, the droplets of the aerosolized catalyst support precursor mixture 109 may not dry sufficiently and may be left unreacted such that the catalyst support particles 114 are not formed. Conversely, if the residence time is too great, energy is wasted and the catalyst support particles 114 may be lost to the furnace walls or grow too large in size due to collisions with other catalyst support particles 114. Additionally, drying the droplets of the aerosolized catalyst support precursor mixture 109 too rapidly, such as by decreasing the residence time too much, increasing the temperature in the first heating zone 120 too much, or both, can lead to catalyst support shells, which can collapse under further processing, instead of solid catalyst particles 114, as previously described.

The feed rate of the aerosolized catalyst support precursor mixture 109 into and through the first heating zone 120 may be determined by the flowrate of the carrier gas 112. In general, the faster the flowrate of the carrier gas 112, the higher the feed rate of the aerosolized catalyst support precursor mixture 109 into the first heating zone 120. The carrier gas 112 flowrate may also influence the residence time of the aerosolized catalyst support precursor mixture 109 in the first heating zone 120. Increasing the carrier gas 112 flowrate may reduce the residence time. Conversely, decreasing the carrier gas 112 flowrate may increase the residence time. In embodiments, the carrier gas 112 flowrate may be sufficient to maintain an aerosolized and fluidized flow of droplets of the aerosolized catalyst support precursor mixture 109 through the first heating zone 120 but not so much that the residence time of the aerosolized catalyst support precursor mixture 109 is not sufficient to fully form the catalyst support particles 114. In some embodiments, the carrier gas 112 flowrate may be sufficient to achieve a residence time of the aerosolized catalyst support particles 114 in the first heating zone 120 and the second heating zone 130 of from 0.1 seconds to 10 seconds, from 0.1 seconds to 9 seconds, from 0.1 seconds to 8 seconds, 0.1 second to 6 seconds, from 0.1 second to 4 seconds, from 0.5 seconds to 10 second, from 0.5 seconds to 9 seconds, from 0.5 seconds to 8 seconds, from 0.5 seconds to 6 seconds, from 0.5 seconds to 4 seconds, from 1 second to 10 seconds, from 1 second to 9 seconds, from 1 second to 8 seconds, from 1 second to 6 seconds, from 1 second to 4 seconds, from 2 seconds to 10 seconds, from 2 seconds to 9 seconds, from 2 seconds to 8 seconds, from 2 seconds to 6 seconds, or from 2 seconds to 4 seconds. For embodiments in which the aerosolizing unit comprises one or a plurality of ultrasonic transducers, the carrier gas 112 flowrate may be from 1.25 liters per min (L/min) to 3.75 L/min per transducer. Alternatively, the carrier gas 112 flowrate may be greater than 3.75 L/min or less than 1.25 L/min depending on the size of the equipment (i.e., first heating zone 120, second heating zone 130, aerosolizing unit 110, etc.) of the aerosol processing system 100.

Referring again to FIG. 1, once the catalyst support particles 114 are formed, the aerosol 113 may comprise the carrier gas 112 and the catalyst support particles 114. The aerosol 113 may then be passed to a second heating zone 130 where a catalytically active compound may be deposited onto the surface of the plurality of catalyst support particles 114. The second heating zone 130 may be in tandem with the first heating zone 120, meaning that the second heating zone 130 is positioned downstream of the first heating zone 120. The catalyst support particles 114 may be passed to and through the second heating zone 130 by the carrier gas 112. In some embodiments, the second heating zone 130 may be a second furnace, more specifically, a region in a second furnace. Alternatively, the second heating zone 130 may comprise another region of the first furnace separate from the first heating zone 120. In some embodiments, the second heating zone 120 may be a second section of a reaction tube that extends through a second furnace or another region of the first furnace. In the second heating zone 130, the catalyst support particles 114 may be contacted with the catalytically active compound precursor vapor 136. Although the aerosol processing systems 100 and methods are described in this disclosure as having at least a first heating zone 120 and a second heating zone 130, it is contemplated that the aerosol processing systems 100 may have more than two heating zones. Additionally, it is contemplated that the first heating zone 120, the second heating zone 130, or both may include multiple temperature regions, which may be independently controlled at different temperatures.

As illustrated in FIG. 1, in some embodiments, the second heating zone 130 may include a source 132 of the catalytically active compound precursor vapor 136. In the embodiment shown in FIG. 1, the source 132 of the catalytically active compound precursor vapor 136 may include a crucible or other open vessel containing a catalytically active compound precursor. Heat from the second heating zone 130 may be transferred to the source 132 and the catalytically active compound precursor contained within the source 132. The heat from the second heating zone 130 may cause the catalytically active compound precursor to vaporize to form the catalytically active compound precursor vapor 136. Alternatively, in some embodiments, the source 132 of the catalytically active compound precursor vapor 136 may be heated independently of the second heating zone 130. For example, the source 132 may include a supplemental heat source that may be controlled independent of the second heating zone 130. The catalytically active compound precursor may transfer/vaporize into the vapor phase through evaporation, sublimation, reaction/decomposition, melting, or combinations of these, for example. The catalytically active compound precursor vapor 136 may distribute throughout the second heating zone 130. In embodiments, a catalytically active compound precursor stream 134 comprising the catalytically active compound precursor may be continuously introduced to the source 132 to maintain continuous generation of the catalytically active compound precursor vapor 136 in the second heating zone 130.

The catalytically active compound precursor 134 may comprise a metal, metal salt, metallate such as a metal oxide for example, other catalytically active compound precursors, or combinations of these. The catalytically active compound precursor 134 may be any metal or metal oxide that can be vaporized to produce the catalytically active compound precursor vapor 136. Alternatively, the catalytically active compound precursor 134 may be a metal salt that can be solubilized in a diluent and atomized or aerosolized. In some embodiments, the catalytically active compound precursor 134 may include a metal such as platinum, gold, palladium, rhodium, iridium, chromium, other metal, or combinations of these. Alternatively, the catalytically active compound precursor 134 may include a metallate precursor, such as an oxymetallate precursor for example. The metal of the metallate precursor may include one or more than one metals from Groups 6-10 of the IUPAC Periodic Table. In some embodiments, the metal of the metallate precursor may include at least one of molybdenum, rhenium, tungsten, manganese, titanium, cerium, or any combination of these. In some embodiments, the metallate precursor may be a tungstate or tungsten oxide, such as tungsten (IV) oxide, tungsten (VI) oxide, other tungsten oxides, or combinations of tungsten oxides. Examples of tungstates may include, but are not limited to ammonium metatungstate ($(NH_4)_6H_2W_{12}O_{40}$), tungstic acid, phosphotungstic acid, sodium tungstate, other tungstate precursor, or combinations of these. In some embodiments, the catalytically active compound precursor 134 may include a tungsten-containing compound that vaporizes or decomposes into a vapor containing tungsten at a temperature of from 150° C. to 1500° C. In some embodiments, the catalytically active compound precursor 134 may include at least one of tungsten metal, tungsten (IV) oxide, tungsten (VI) oxide, tungstic acid, tungstophosphoric acid, ammonium metatungstate, tungsten oxychloride, tungsten hexachloride, other tungsten-containing compounds, or combinations of these.

The catalytically active compound precursor may be continuously introduced to the source 132 of the catalytically active compound precursor vapor 136 in the second heating zone 130. The second heating zone 130 may be maintained at a temperature sufficient to vaporize the catalytically active compound precursor to generate the catalytically active compound precursor vapor 136 within the second heating zone 130. In some embodiments, the temperature of the second heating zone 130 may be maintained at a temperature sufficient to maintain a steady state of the catalytically active compound precursor vapor 136 in the second heating zone 130. In some embodiments, the second heating zone 130 may be maintained at a temperature of from 600° C. to 1400° C. so that a temperature of the catalytically active compound precursor vapor 136 in the second heating zone 130 is from 600° C. to 1400° C. In other embodiments, the second heating zone 130 may be maintained at a temperature of from 600° C. to 1400° C., from 600° C. to 1350° C., from 600° C. to 1300° C., from 600° C. to 1200° C., from 600° C. to 1100° C. In embodiments, the temperature of the second heating zone 130 may be controlled to control the vaporization rate of the catalytically active compound precursor 134.

In some embodiments, the second heating zone 130 may be operated at ambient pressure. Alternatively, the second heating zone 130 may also be operated at positive pressure or under a vacuum. A vapor pressure of the catalytically active compound precursor vapor 136 in the second heating zone 130 may be controlled by controlling the temperature of the second heating zone 130, the source 132 of the catalytically active compound precursor vapor 136, or both. The vapor pressure of the catalytically active compound precursor vapor 136 may also be controlled by controlling the flow rate of carrier gas 112 through the second heating zone 130. Thus, the aerosol processing method may not require that the vapor pressure of the catalytically active compound precursor 136 be maintained at a high level for an extended period of time through the application of a partial vacuum in the second heating zone 130.

In embodiments, the residence time of the catalyst support particles 114 in the second heating zone 130 may be sufficient to maintain steady state vaporization of the catalytically active compound precursor vapor 136 into the vapor phase in the second heating zone 130. For example, in some embodiments, the residence time of the catalyst support particles 114 in the second heating zone 130 may be sufficient to enable the catalytically active compound precursor 134 to vaporize uniformly from the source 132 and distribute through the second heating zone 130. In some embodiments, the residence time of the catalyst support particles 114 in the second heating zone 130 may be from 0.1 seconds to 10 seconds. In other embodiments, the residence time of the catalyst support particles 114 in the second heating zone 130 may be from 0.1 seconds to 9 seconds, from 0.1 seconds to 8 seconds, 0.1 second to 6 seconds, from 0.1 second to 4 seconds, from 0.5 seconds to 10 second, from 0.5 second to 9 seconds, from 0.5 seconds to 8 seconds, from 0.5 seconds to 6 seconds, from 0.1 second to 0.4 seconds, from 1 second to 10 seconds, from 1 second to 9 seconds, from 1 seconds to 8 second, from 1 second to 6 seconds, from 1 second to 4 seconds, from 2 seconds to 10 seconds, from 2 seconds to 9 seconds, from 2 seconds to 8 seconds, from 2 seconds to 6 seconds, or from 2 seconds to 4 seconds.

The catalyst support particles 114 may be contacted with the catalytically active compound precursor vapor 136 in the second heating zone 130. Upon exiting the second heating zone 130, the catalytically active compound precursor vapor 136 and the catalyst support particles 114 may be cooled. In some embodiments, the aerosolized flow of catalyst support particles 114 and catalytically active compound precursor vapor 136 may be cooled at a controlled rate to a temperature of less than 120° C., such as a temperature from 20° C. to 120° C. A desired cooling rate of the aerosolized flow of catalyst support particles 114 and catalytically active compound precursor vapor 136 may be achieved by modifying the residence time of the materials in the second heating zone 130 or by changing the distance between the second heating zone 130 and the separator 140. Additionally, the cooling rate of the aerosolized flow of catalyst support particles 114 and catalytically active compound precursor vapor 136 may be controlled using fans or heat exchangers or by changing the insulation materials. Further, the cooling rate of the aerosolized flow of catalyst support particles 114 and catalytically active compound precursor vapor 136 may be controlled by controlling a temperature of the separator 140.

As the catalytically active compound precursor vapor 136 cools, the catalytically active compound precursor vapor 136 may condense. As previously described, the catalytically active compound precursor vapor 136 may condense directly onto the surface of the catalyst support particles 114 or onto catalytically active compound previously condensed on the surface of the catalyst support particles 114. In some embodiments, the catalytically active compound precursor vapor 136 may condense on the outer surfaces of the catalyst support particles 114 and on surfaces of the catalyst support particles 114 that are accessible to gases and vapors, such as porous regions of the catalyst support particles 114 for example. Alternatively or additionally, the catalytically active compound precursor vapor 136 may condense onto itself (homogeneous nucleation) to create clusters or particles of catalytically active compound that may then diffuse to the catalyst support particles 114 and deposit onto the surface of the catalyst support particles 114. The clusters or particles of catalytically active compound may deposit onto the outer surfaces of the catalyst support particles 114 and on surfaces of the catalyst support particles 114 that are accessible to gases and vapors.

Condensation of the catalytically active compound precursor vapor 134 results in formation of the catalyst 101 having individual atoms, molecules, clusters, or particles of the catalytically active compound deposited on the catalyst support particles 114. The individual atoms, molecules, clusters, or particles of the catalytically active compound may be deposited on the surfaces of the catalyst support particles 114 that are accessible to the gases and vapors. For example, the catalytically active compound may be deposited on an outermost surface of the catalyst support particles 114, on the walls of pores in an outer portion of the catalyst support particles 114 in fluid communication with the outer surface of the catalyst support particles 114, or both. The interior portions of the catalyst support particles 114 may be substantially free of the catalytically active compound. As used in this disclosure, the term "substantially free" of a component means less than 0.1 weight percent of that component in a particular portion of a catalyst, stream, or reaction zone. For example, the interior portions of the catalyst support particles 114 may have less than 0.1 weight percent catalytically active compound, based on the total weight of the catalyst 101. The interior portions of the catalyst support particles 114 refers to the portions of the catalyst support particles 114 that are inaccessible to gases and vapors. For example, the interior of the catalyst support particles 114 includes the solid portions of the catalyst support particles 114 and internal pores of the catalyst support particles 114 that are not in fluid communication with the outer surface of the catalyst support particles 114.

In some embodiments, the resulting catalyst 101 particles may have 100% of the catalytically active compound deposited only on the surfaces of the catalyst support particles 114 that are accessible to vapors and gases, which may include the outermost surface of the catalyst support particles 114, walls of pores in an outer portion of the catalyst support particles 114 in fluid communication with the outer surface of the catalyst support particles 114, or both. The catalytically active compound may be deposited on enough of the surfaces of the catalyst support particles 114 that are accessible to vapors and gases to provide sufficient catalytic activity to the catalyst 101 particles. However, depositing the catalytically active compound over too great of a percentage of the surfaces of the catalyst support particles 114 that are accessible to vapors and gases may result in the catalytically active compound forming larger clusters or agglomerates, which may reduce the catalytic activity of the catalyst 101 particles. In some embodiments, the catalyst 101 particles may have the catalytically active compound deposited on greater than or equal to 1% of the surfaces of the catalyst support particles 114 that are accessible to vapors and gases, greater than or equal to 5% of the surfaces of the catalyst support particles 114 that are accessible to vapors and gases, greater than or equal to 10% of the surfaces of the catalyst support particles 114 that are accessible to vapors and gases, or even greater than or equal to 20% of the surfaces of the catalyst support particles 114 that are accessible to vapors and gases. In other embodiments, the catalyst 101 particles may have the catalytically active compound deposited on less than or equal to 50% of the surfaces of the catalyst support particles 114 that are accessible to vapors and gases, less than or equal to 40% of the surfaces of the catalyst support particles 114 that are accessible to vapors and gases, less than or equal to 30% of the surfaces of the catalyst support particles 114 that are accessible to vapors and gases, less than or equal to 20% of the surfaces of the catalyst support particles 114 that are accessible to vapors and gases, or even less than or equal to 10% of the surfaces of the catalyst support particles 114 that are accessible to vapors and gases. For example, in some embodiments the catalyst 101 particles may have the catalytically active compound deposited on from 1% to 50% of the surfaces of the catalyst support particles 114 that are accessible to vapors and gases, such as from 1% to 40%, from 1% to 30%, from 1% to 20%, from 1% to 10%, from 1% to 5%, from 5% to 50%, from 5% to 40%, from 5% to 30%, from 5% to 20%, from 5% to 10%, from 10% to 50%, from 10% to 40%, from 10% to 30%, from 10% to 20%, from 20% to 50%, from 20% to 40%, or from 20% to 30% of the surfaces of the catalyst support particles 114 that are accessible to vapors and gases.

The resulting catalyst 101 particles may have the catalytically active compound that is more dispersed, less clustered, or both, on the surfaces of the catalyst support particles 114 that are accessible to vapors and gases compared to conventional catalysts synthesized by wet impregnation methods or other similar methods. As used in this disclosure, the term "dispersed" refers to the catalytically active compound being spread out over the surfaces of the catalyst support particles 114 that are accessible to vapors and gases, as compared to being concentrated in larger clusters and agglomerates. For example, the "most-dispersed" state would comprise a mono-layer of molecules of the catalytically active compound deposited on the surfaces of the catalyst support particles 114.

The degree to which the catalytically active compound is dispersed on the surfaces of the catalyst support particles 114 accessible to vapors and gases may be evaluated by determining the average particle size of the catalytically active compound deposited on surfaces of the catalyst support particles 114. The average particle size of the catalytically active compound may be determined using, for example, Small Angle X-Ray Scattering (SAXS) as subsequently discussed in this disclosure, or alternatively by transmission electron microscopy. As used in this disclosure in relation to the catalytically active compound deposited on surfaces of the catalyst support particles accessible to vapors and gases, the "average particle size" refers to an average radius of the crystals, clusters, or agglomerates, of the catalytically active compound deposited on the surfaces of the catalyst support particles accessible to vapors and gases. The average particle size includes the radii of single atoms and single molecules of the catalytically active compound deposited as single atoms or single molecules on the surfaces of the catalyst support particles. In general, the smaller the average particle size of the catalytically active compound deposited on the surfaces of the catalyst support particles 114 the more dispersed the catalytically active compound is and the less clustered the catalytically active compound is. Greater average particle size of the catalytically active compound indicates that the deposition process has resulted in additional clustering or agglomeration of the catalytically active compound into larger-sized crystals, clusters, or agglomerates, which may reduce the degree to which the catalytically active compound is dispersed on the surfaces of the catalyst support particles 114 that are accessible to vapors and gases.

In some embodiments, the average particle size of the catalytically active compound deposited on the surfaces of the catalyst support particles 114 that are accessible to vapors and gases may be less than the average particle size of the catalytically active compound deposited on the catalyst support particles 114 by wet impregnation or other conventional process. For example, in some embodiments, the average particle size (average radius) of the catalytically active compound deposited on the surfaces of the catalyst support particles 114 that are accessible to vapors and gases may be less than or equal to 2.5 nanometers (nm), less than or equal to 2 nm, less than or equal to 1.5 nm, or less than or equal to 1 nm. In other embodiments, the average particle size of the catalytically active compound deposited on the surface of the catalyst support particles 114 that is accessible to vapors and gases may be greater than or equal to an atomic radius of a single atom of the catalytically active compound or greater than or equal to a molecular radius of a single molecule of the catalytically active compound. In some embodiments, the average particle size of the catalytically active compound deposited on the surfaces of the catalyst support particles 114 that are accessible to vapors and gases may be from 0.1 nm to 2.5 nm, from 0.1 nm to 2 nm, from 0.1 nm to 1.5 nm, from 0.1 nm to 1 nm, from 0.1 nm to 0.5 nm, from 0.5 nm to 2.5 nm, from 0.5 nm to 2 nm, from 0.5 nm to 1.5 nm, from 0.5 nm to 1 nm, from 1 nm to 2.5 nm, from 1 nm to 2 nm, or from 1 nm to 1.5 nm.

The average crystalline size of the catalytically active compound may be determined using the SAXS method to measure the average radius of the catalytically active compound crystals and/or agglomerates using a Bruker NANO-STAR™ small angle X-ray scattering system with the x-ray source operating at 45 kilovolts (kV) and 650 microangtroms (μA). Samples are placed in quartz capillary tubes having an outer diameter of 1.5 millimeter (mm), a length of 80 mm length, and a wall thickness of 0.01 mm. Quartz capillary tubes may be obtained from the Charles Supper Co., of Natick, Mass., USA. After placing the samples in the capillary tubes, the capillary tubes are sealed with CRYTOSEAL™, available from Fisher Scientific, Fairlawn, N.J., USA, and hot-melt adhesive available from Ted Pella, Redding, Calif., USA. Each sealed quartz capillary tube is placed in a sample mount that orients the capillary tube in the sample chamber upright and perpendicular to the beam. The sample chamber is placed under vacuum to eliminate parasitic scattering from air. Two-dimensional intensity data are collected by averaging the scattered X-ray intensity over a 30 minute window.

Intensity patterns are azimuthally averaged and corrected for background and indirect transmission using the appropriate blank and control sample data and assuming a glassy carbon transmission value of 0.1400. Scattering data curves are initially fit using a Porod analysis to provide a first approximation of the particle size. Direct fitting is then performed using the Bruker Diffrac.SAXS software over a q range of from 0.1357 per angstrom ($Å^{-1}$) to 0.30154 $Å^{-1}$ and employing a theoretical scattering function for polydisperse spheres. The size and size distribution of the particles is determined assuming a lognormal distribution of core radii assuming no relevant interactions between the particles. Direct modelling results are replicated via three separate blind, independent fits, and the extremity results from these fits are used to generate the reported ranges for particle radius. The SAXS method is further described in Wojciech, Szczerba et al., "SAXS Analysis of Single- and Multi-Core Iron Oxide Magnetic Nanoparticles," J Appl Crystallogr. 2017 Apr. 1; 50(Pt 2): 481-488 (Published online 2017 Mar. 14). It is understood that other methods and technologies may be used to determine the average particle size of the catalytically active compound.

Condensation of the catalytically active compound precursor vapor 136 may occur through a decrease in the temperature of the catalytically active compound precursor vapor 136 resulting from cooling as catalyst support particles 114 and the catalytically active compound precursor vapor 136 exit the second heating zone 130. The carrier gas 112 flowrate may influence the rate of cooling of the catalytically active compound precursor vapor 136 and thus the rate of condensation. In some embodiments, the carrier gas 112 flowrate may be controlled to control the cooling rate of the catalytically active compound precursor vapor 136. Additionally, a curvature of the catalyst support particle 114 or clusters or nanoparticles of the catalytically active compound may depress the vapor pressure of the catalytically active compound precursor vapor 136 locally in the vicinity of the catalyst support particle 114 or clusters/nanoparticles of the catalytically active compound, thereby causing condensation of the catalytically active compound precursor vapor 136 at higher temperatures compared to condensation resulting from cooling. Thus, condensation of the catalytically active compound precursor vapor 136 may occur at the higher temperatures within the second heating zone 130 before the catalytically active compound precursor vapor 136 exits the second heating zone 130.

The amount of the catalytically active compound condensed onto the surfaces of the catalyst support particles 114 may be controlled by controlling the concentration of the catalyst support material 114, the selection of and temperature of the catalytically active compound precursor in the second heating zone 130, such as by controlling the temperature of the second heating zone 130, the temperature of the source 132 of the catalytically active compound precursor, or both. Controlling the temperature of the second heating zone 130, source 132, or both influences the vaporization rate of the catalytically active compound precursor. The amount of catalytically active compound condensed onto the surfaces of the catalyst support particles 114 may also be controlled by controlling the flowrate of the aerosol 113 through the second heating zone 130, the concentration of the catalyst support precursor 104 in the catalyst support precursor mixture 108, the particle size of the catalyst support particles 114, the temperature of the aerosol 113 during deposition, and the final temperature of the aerosol at the separator 140, the concentration of the catalyst support particles 114 in the aerosol 113, or combinations of these.

The deposition rate of the catalytically active compound onto the surfaces of the catalyst support particles may also be controlled by controlling the temperature of the catalytically active compound precursor in the second heating zone 130, the position of the source 132 of the catalytically active compound precursor within the second heating zone 130, the flowrate of the aerosol 113 through the aerosol processing system 100, the concentration of the catalyst support precursor 104 in the catalyst support precursor mixture 108, the cooling rate at the exit of the second heating zone 130, the concentration of the catalyst support particles 114 in the aerosol 113, the particle size of the catalyst support particles 114 in the aerosol 113, or combinations of these.

In some embodiments, the catalytically active compound precursor 134 may be a gas that may decompose in the second heating zone 130 to deposit the catalytically active compound onto the surfaces of the catalyst support particles 114. In these embodiments, the catalytically active compound precursor gas may be introduced directly to the second heating zone 130. Heat from the second heating zone 130 may cause the catalytically active compound precursor gas to decompose to produce the catalytically active compound, which may then be deposited on the surfaces of the catalyst support particles 114.

The catalyst 101 may have an amount of the catalytically active compound deposited on the surface of the catalyst 101 sufficient to provide a desired level of catalytic activity to the catalyst 101. In some embodiments, the catalyst 101 may have from 0.0002 weight percent to 20 weight percent catalytically active compound, based on the total weight of the catalyst 101 particles. In other embodiments, the catalyst 101 may have from 0.0002 weight percent to 10 weight percent, from 0.0002 weight percent to 5 weight percent, from 0.0002 weight percent to 1 weight percent, from 0.0002 weight percent to 0.5 weight percent, from 0.001 weight percent to 20 weight percent, from 0.001 weight percent to 10 weight percent, from 0.001 weight percent to 5 weight percent, from 0.001 weight percent to 1 weight percent, from 0.001 weight percent to 0.5 weight percent, from 0.01 weight percent to 20 weight percent, from 0.01 weight percent to 10 weight percent, from 0.01 weight percent to 5 weight percent, from 0.01 weight percent to 1 weight percent, from 0.01 weight percent to 0.5 weight percent, from 0.1 weight percent to 20 weight percent, from 0.1 weight percent to 10 weight percent, from 0.1 weight percent to 5 weight percent, from 0.1 weight percent to 1 weight percent, from 0.1 weight percent to 0.5 weight percent, from 0.5 weight percent to 20 weight percent, from 0.5 weight percent to 10 weight percent, from 0.5 weight percent to 5 weight percent, from 0.5 weight percent to 1 weight percent, from 1 weight percent to 20 weight percent, from 1 weight percent to 10 weight percent, or from 1 weight percent to 5 weight percent catalytically active compound, based on the total weight of the catalyst. In some embodiments, the catalyst 101 may have less than or equal to 10 weight percent, less than or equal to 5 weight percent, less than or equal to 1 weight percent, less than or equal to 0.5 weight percent, or even less than or equal to 0.4 weight percent catalytically active compound, based on the total weight of the catalyst 101 particles.

In embodiments, the aerosol processing system 100 includes the separator 140 for separating the catalyst 101 from the carrier gas 112 and collecting the catalyst 101. The carrier gas 112 and the catalyst 101 particles entrained in the carrier gas 112 pass out of the second heating zone 120 and into the separator 140. The method of synthesizing the catalyst 101 includes separating the catalyst 101 from the carrier gas 112 and collecting the catalyst 101. In some embodiments, the carrier gas 112 may be passed from the separator 140 to the atmosphere without further treatment. Alternatively, the carrier gas 112 exiting the separator may be further processed to recover residual constituents of the process, such as catalytically active compound precursor vapors 136, organic solvents from the catalyst support precursor mixture, or other contaminants, for example. In some embodiments, the carrier gas 112 passed out of the separator 140 is substantially free of chlorine-containing compounds. As an example, the carrier gas 112 exiting the separator 140 may have less than 0.1 weight percent chlorine-containing compounds.

In some embodiments, the separator 140 may be a cyclone separator, an electrostatic precipitator, or a filter that is used to separate the catalyst 101 from the flow of the carrier gas 112 exiting the second heating zone 130. An example filter may comprise borosilicate fibers bound with polyvinylidene fluoride (PVDF) configured to have a desired efficiency at capturing 0.01 micron (μm) particles. Another example filter may consist of quartz bound with an inorganic resin that can tolerate higher operating temperatures. The filter may also be comprised of any commercially available bag house filter material. In selecting a filter, there is a desire to balance pore size of the filter to sufficiently collect the catalyst 101 particles with the resulting pressure increase which results as the filter collects catalyst 101 particles and at temperatures suitable for collection. As the filter begins to clog and a particle cake forms, the filter becomes a more efficient filter and the pressure starts to rise. In operation, the resulting pressure rise may be used as an indicator of the quantity of catalyst 101 collected within the filter. Additionally, the filter material may be temperature stable at temperatures greater than or equal to the temperature of the aerosol 113 exiting the second heating zone 130 to prevent the filter material from undergoing combustion.

As described above, FIG. 1 illustrates vaporization of the catalytically active compound precursor 134 by positioning the source 132 of the catalytically active compound precursor 134 in the second heating zone 130 and vaporizing the catalytically active compound precursor 134 in the second heating zone 130. Alternatively, as shown in FIGS. 2-6, other embodiments of aerosol processing systems may utilize alternative methods of providing the catalytically active compound precursor 134 or catalytically active compound to the second heating zone 130.

Figure 2:
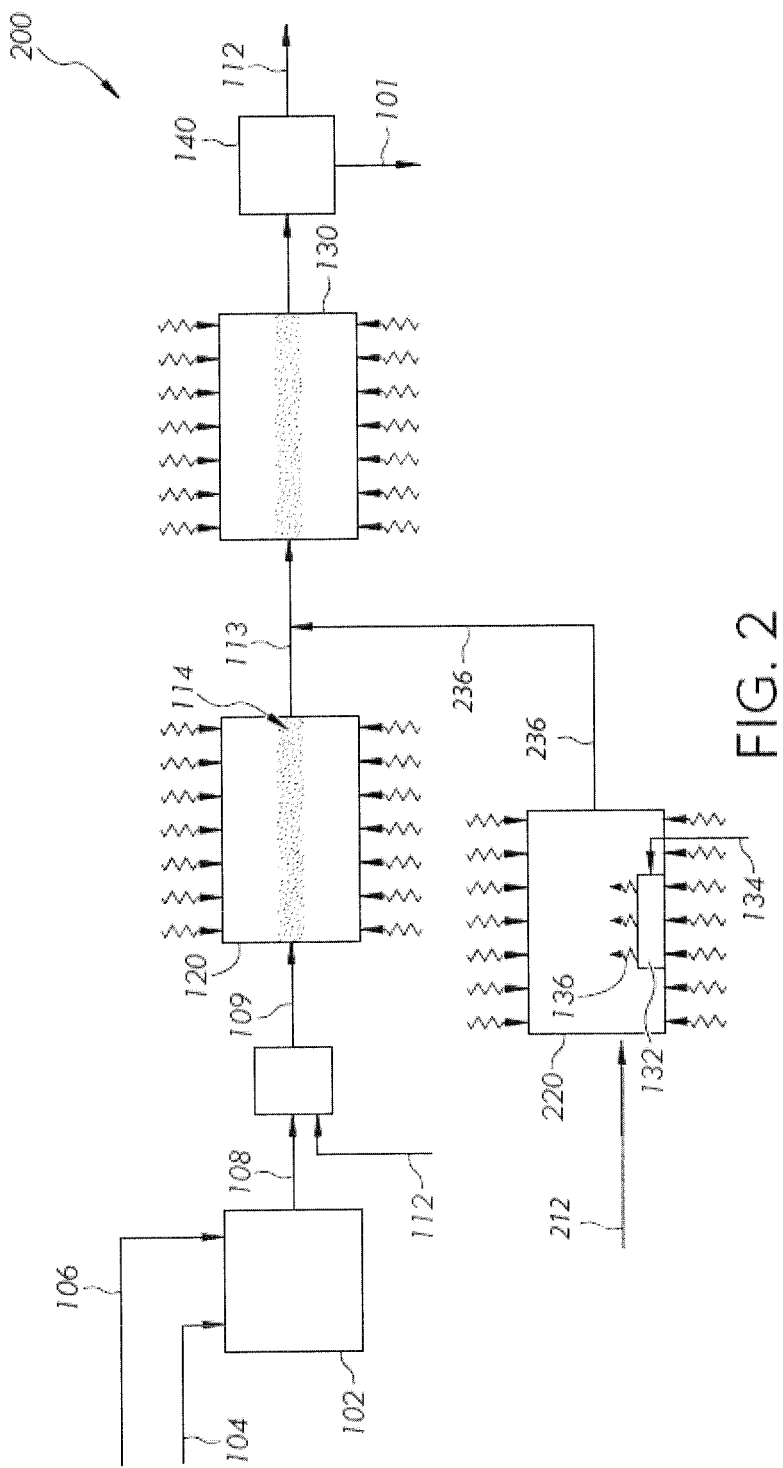
FIG. 2 schematically depicts another aerosol processing system, in accordance with one or more embodiments of the present disclosure.

Referring now to FIG. 2, an aerosol processing system 200 may include a third heating zone 220, and the source 132 of the catalytically active compound precursor vapor 136 may be positioned within the third heating zone 220. The aerosol processing system 200 may also include the vessel 102, the aerosolizing unit 110, the first heating zone 120, the second heating zone 130, and the separator 140 previously described for the aerosol processing system 100 of FIG. 1. As shown in FIG. 2, the third heating zone 220 of aerosol processing system 200 may be parallel to the first heating zone 120 and may be upstream of the second heating zone 130. In some embodiments, the third heating zone 220 may be a third furnace, more specifically, a region in a third furnace.

In FIG. 2, the source 132 of the catalytically active compound precursor vapor 136 may include a crucible or other open vessel containing a catalytically active compound precursor. Heat from the third heating zone 220 may be transferred to the source 132 and the catalytically active compound precursor contained within the source 132. The heat from the third heating zone 220 may cause the catalytically active compound precursor to vaporize to form the catalytically active compound precursor vapor 136. Alternatively, in some embodiments, the source 132 may be heated independently of the third heating zone 220. The catalytically active compound precursor may transfer/vaporize into the vapor phase through evaporation, sublimation, reaction/decomposition, melting, or combinations of these, for example. In embodiments, a catalytically active compound precursor stream 134 comprising the catalytically active compound precursor may be continuously or periodically introduced to the source 132 to maintain continuous generation of the catalytically active compound precursor vapor 136 in the third heating zone 220.

A carrier gas 212 may be introduced to the third heating zone 220 to carry the catalytically active compound precursor vapor 136 to the second heating zone 130. The carrier gas 212 may be any of the carrier gases previously described for carrier gas 112. The carrier gas 212 may be the same as carrier gas 112 or different than carrier gas 112. Stream 236 may include the catalytically active compound precursor vapor 136 carried by the carrier gas 212 and may be passed out of the third heating zone 220. In some embodiments, the stream 236 may be combined with the aerosol 113 passing out of the first heating zone 120 upstream of the second heating zone 130. In these embodiments, the aerosol 113 and the stream 236 are mixed and the catalytically active compound precursor vapor 136 in stream 236 and the aerosol 113 are contacted before being passed to the second heating zone 130. Alternatively, the aerosol 113 and the stream 236 may be individually passed to the second heating zone 130. In these embodiments, the aerosol 113 and the catalytically active compound precursor vapor 136 in stream 236 are mixed and contacted in the second heating zone 130. Upon exiting the second heating zone 130, the catalytically active compound precursor vapor 136 condenses as previously described in this disclosure to produce the catalyst 101 having the catalytically active compound deposited on the surfaces of the catalyst 101.

Alternatively, in some embodiments, the stream 236 may be cooled upon exiting the third heating zone 220 to produce nanoparticles of the catalytically active compound from the catalytically active compound precursor vapor 136 in the stream 236. The catalytically active compound nanoparticles may then be combined with the aerosol 113. The catalytically active compound nanoparticles may collide with the catalyst support particles 114 of aerosol 113 in the second heating zone 130 to form the catalyst 101 comprising the catalytically active compound nanoparticles deposited on the surfaces of the catalyst 101.

Figure 3:
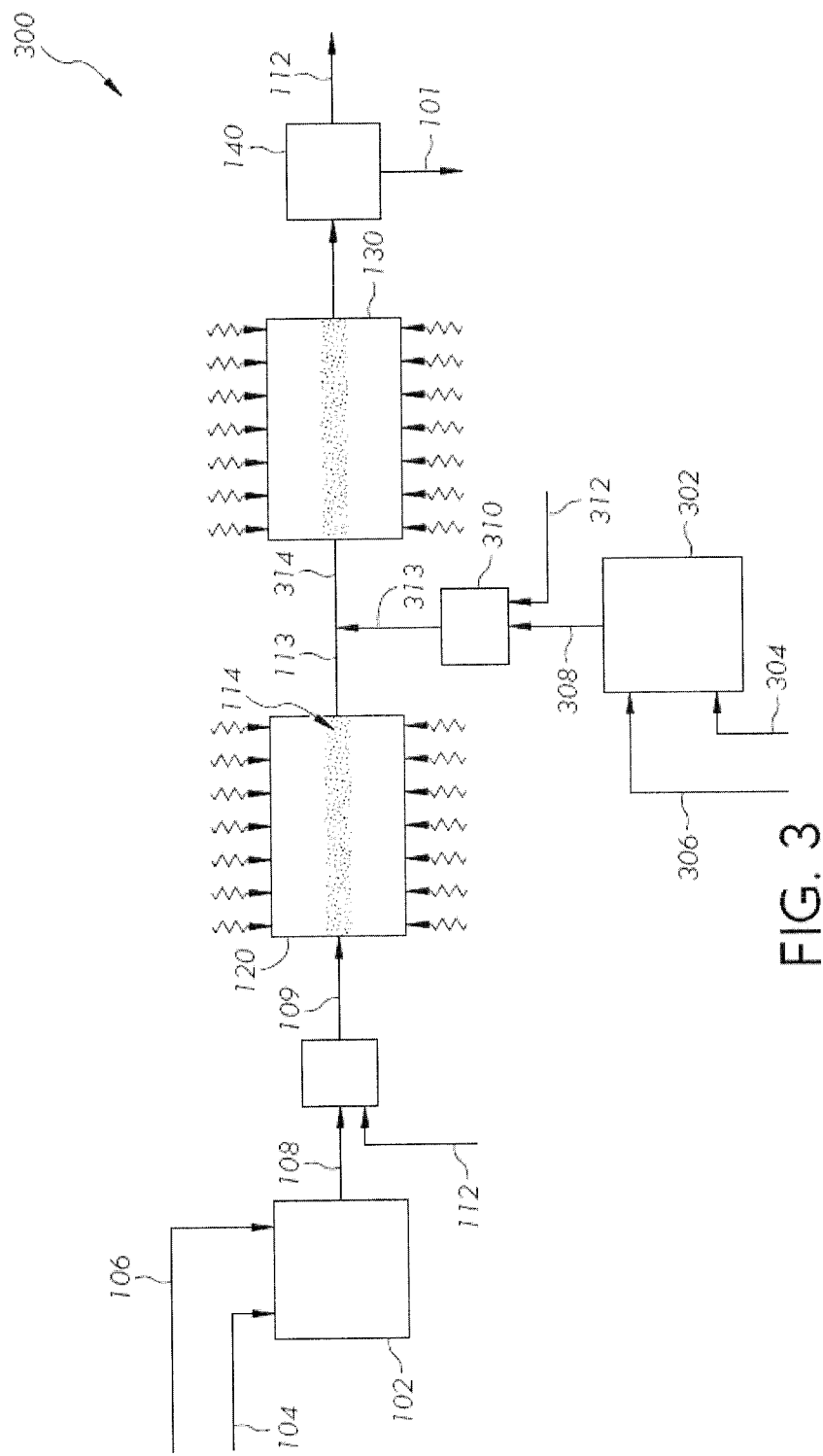
FIG. 3 schematically depicts yet another aerosol processing system, in accordance with one or more embodiments of the present disclosure.

Referring to FIG. 3, in other embodiments, an aerosol processing system 300 may include a supplemental vessel 302 and a supplemental aerosolizing unit 310. The aerosol processing system 300 also includes the vessel 102, the aerosolizing unit 110, the first heating zone 120, the second heating zone 130, and the separator 140 previously described in relation to aerosol processing system 100 of FIG. 1. In the aerosol processing system 300 of FIG. 3, the catalytically active compound precursor 304 may be combined with a diluent 306 in the supplemental vessel 302 to produce a catalytically active compound precursor mixture 308. The catalytically active compound precursor 304 may include any of the materials previously described in relation to catalytically active compound precursors. Additionally, the supplemental diluent 306 and the supplemental carrier gas 312 may be any of the material described above relative to diluent 106 and carrier gas 312, respectively.

The catalytically active compound precursor mixture 308 may be passed to the supplemental aerosolizing unit 310. The supplemental aerosolizing unit 310 may be any of the devices previously described in relation to aerosolizing unit 110. The supplemental aerosolizing unit 310 may aerosolize the catalytically active compound precursor mixture 308 with a supplemental carrier gas 312 to produce a catalyst precursor aerosol 313 comprising droplets of the aerosolized catalytically active compound precursor mixture 308 and the supplemental carrier gas 312. In some embodiments, the catalyst precursor aerosol 313 may be combined with the aerosol 113 passing out of the first heating zone 120 to form combined aerosol stream 314 upstream of the second heating zone 130, as shown in FIG. 3. The combined aerosol stream 314 may then be passed to the second heating zone 220. Alternatively, in other embodiments, the catalyst precursor aerosol 313 and the aerosol 113 may be independently passed to the second heating zone 120 and then combined in the second heating zone 120. The catalyst precursor aerosol 313 may react, dry, or both in the second heating zone 130 to form a plurality of solid particles of the catalytically active compound, and the plurality of solid particles of the catalytically active compound may then collide with the aerosol 113 and deposit onto aerosol 113 to form the catalyst 101. Additionally, the catalyst precursor aerosol 313 may collide with aerosol 113 prior to reacting, drying, or both to form a combined aerosol stream 314 that contains both solid and liquid material. When introduced into the second heating zone 130, the greater temperature in the second heating zone 130 may cause the catalyst precursor aerosol 313 to react, dry, or both on and around catalyst support particles 114 of aerosol 113 to produce the catalyst 101.

Figure 4:
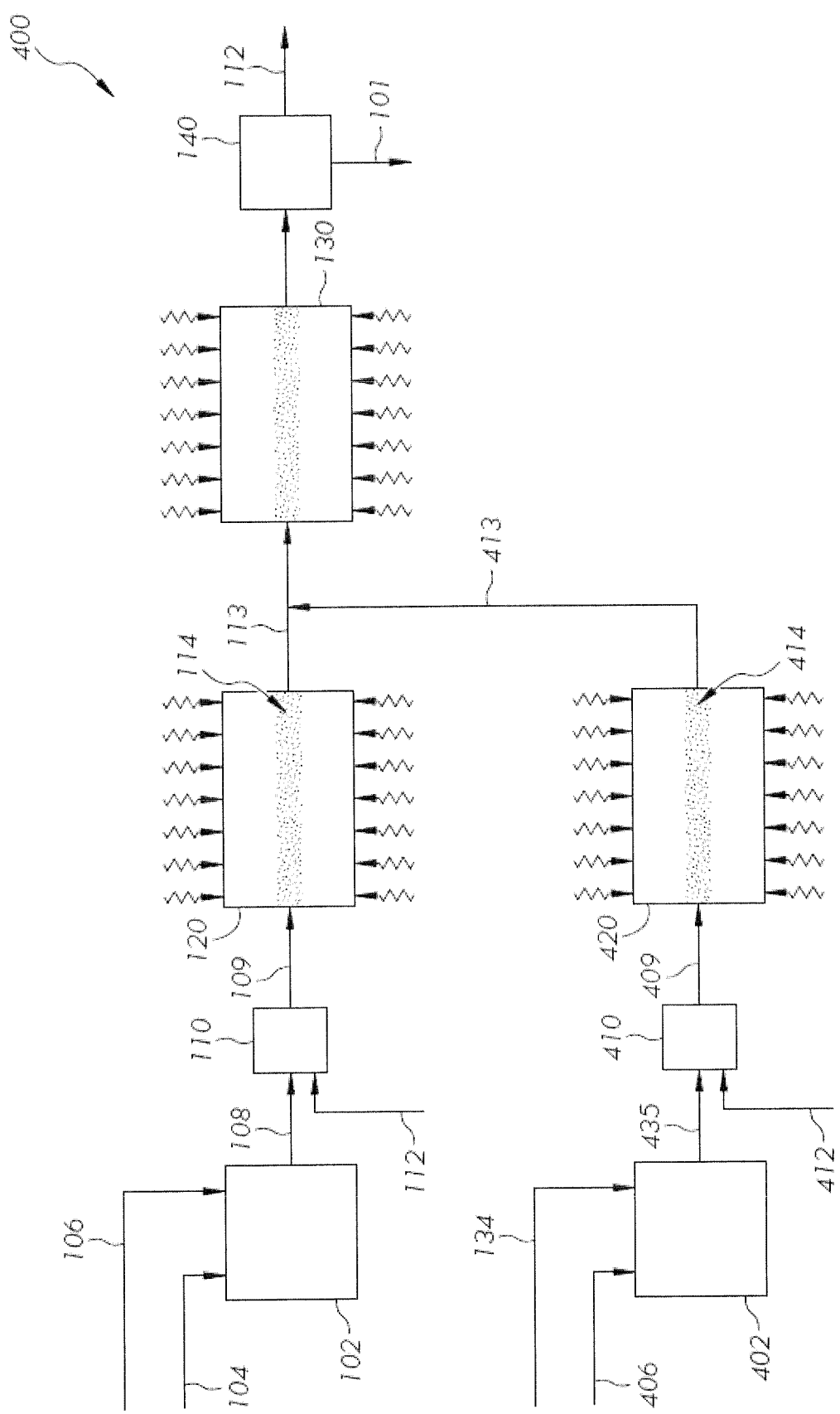
FIG. 4 schematically depicts still another aerosol processing system, in accordance with one or more embodiments of the present disclosure.

Referring to FIG. 4, an aerosol processing system 400 is depicted that includes the vessel 102, the aerosolizing unit 110, the first heating zone 120, the second heating zone 130, and the separator 140 previously described in relation to the aerosol processing system 100 of FIG. 1. As shown in FIG. 4, the aerosol processing system 400 may further include a supplemental vessel 402, a supplemental aerosolizing unit 410 positioned downstream of the supplemental vessel 402, and a third heating zone 420 downstream of the supplemental aerosolizing unit 410. The supplemental vessel 402, the supplemental aerosolizing unit 410, and the third heating zone 420 may be parallel to the vessel 102, aerosolizing unit 110, and first heating zone 120. The catalytically active compound precursor 134 may be combined with a supplemental diluent 406 in the supplemental vessel 402 to produce a catalytically active compound precursor mixture 435. The supplemental diluent 406 may be any of the materials previously described for diluent 106.

The catalytically active compound precursor mixture 435 and a supplemental carrier gas 412 may be introduced to the supplemental aerosolizing unit 410. The supplemental carrier gas 412 may be any of the materials previously described for carrier gas 112. In some embodiments, the supplemental carrier gas 412 may be the same material as the carrier gas 112. The catalytically active compound precursor mixture 435 may be aerosolized in the supplemental aerosolizing unit 410 to produce a catalytically active compound precursor aerosol 409 comprising droplets of the catalytically active compound precursor mixture 435 and the supplemental carrier gas 412. The catalytically active compound precursor aerosol 409 may be passed to and through the third heating zone 420. In the third heating zone 420, the catalytically active compound precursor aerosol 409 may dry, react, or decompose to produce a plurality of catalytically active compound particles 414 aerosolized in the supplemental carrier gas 412. Aerosol 413 may comprise the catalytically active compound particles 414 aerosolized in the supplemental carrier gas 412.

The aerosol 413 may be combined with the aerosol 113 upstream of the second heating zone 130 or in the second heating zone 130. The catalytically active compound particles 414 of aerosol 413 may contact the catalyst support particles 114 of aerosol 113 in the second heating zone 130, which may cause the catalytically active compound particles 414 to deposit onto the surfaces of the catalyst support particles 114 to produce the catalyst 101. Thus, the catalytically active compound particles 414 and the catalyst support particles 114 are formed independently and then combined to deposit the catalytically active compound particles 414 on the surfaces of the catalyst support particles 114.

Figure 5:
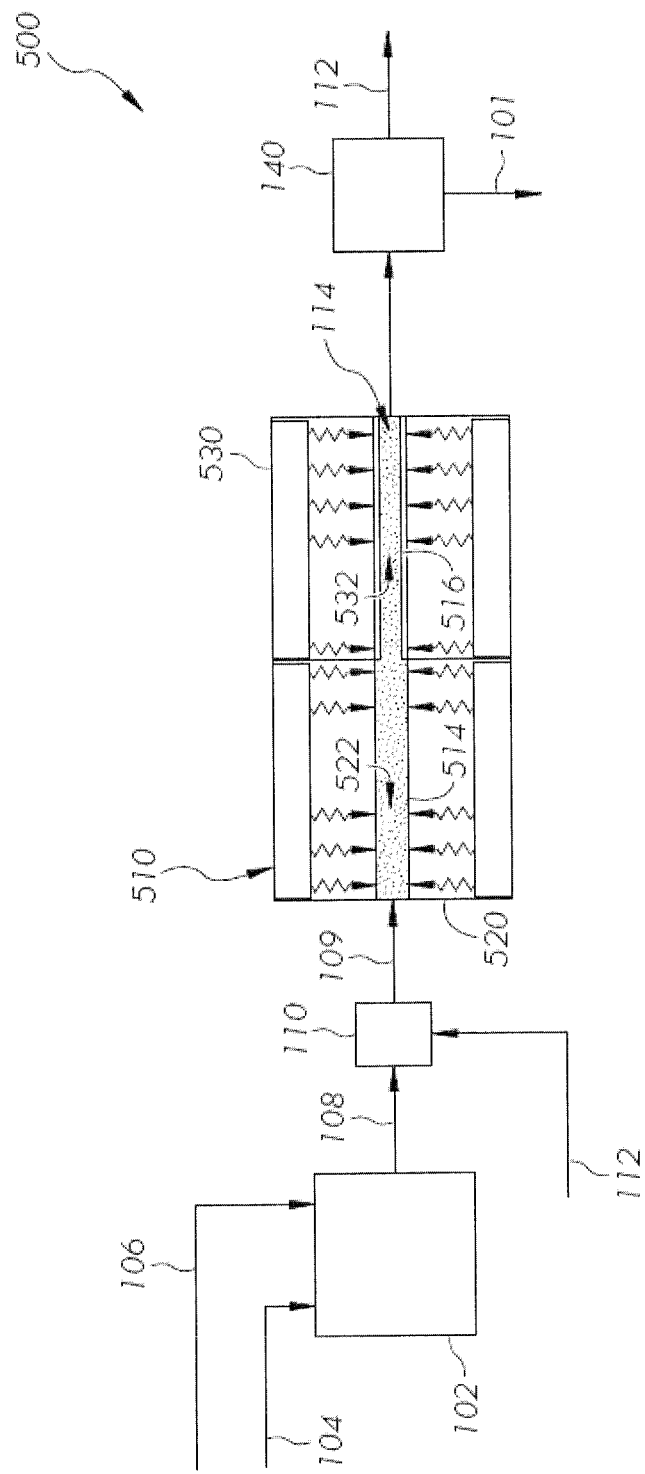
FIG. 5 schematically depicts still another aerosol processing system, in accordance with one or more embodiments of the present disclosure.
Figure 6:
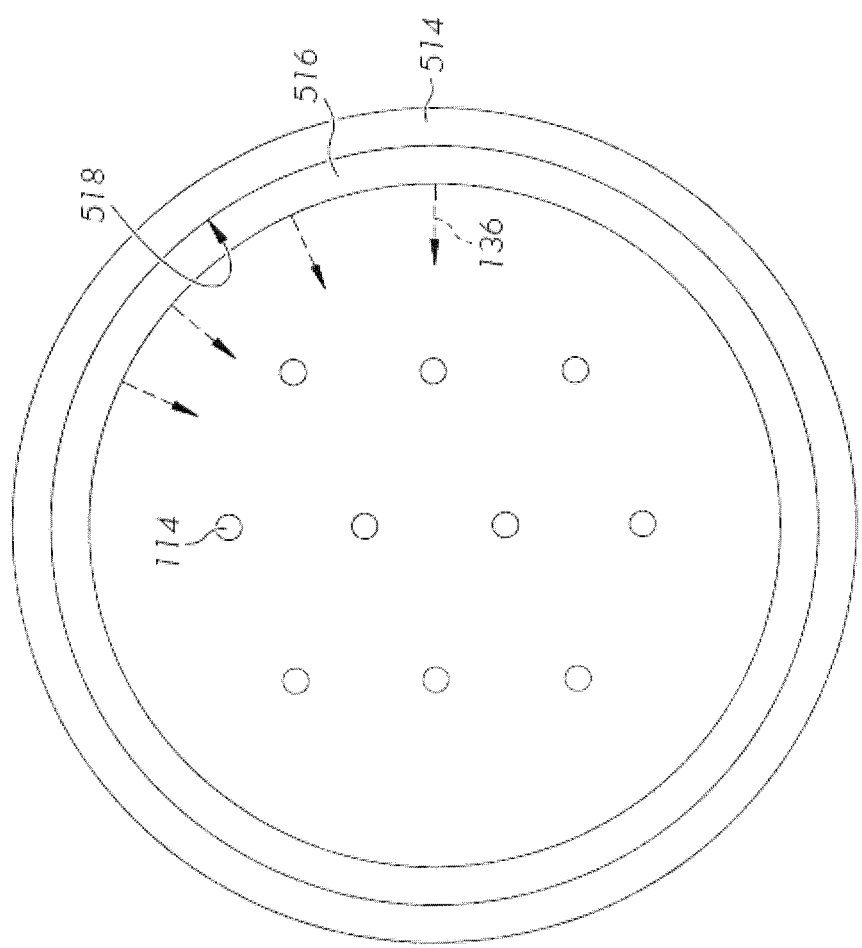
FIG. 6 is cross-section of a reaction tube of the aerosol processing system of FIG. 5, in accordance with one or more embodiments of the present disclosure.

Referring now to FIG. 5, another alternative aerosol processing system 500 for synthesizing the catalyst 101 is depicted. The aerosol processing system 500 of FIG. 5 may include the vessel 102 for preparing the catalyst support precursor mixture 108 from the catalyst support precursor 104, diluent 106, and optionally a dopant. The aerosol processing system 500 may further comprise the aerosolizing unit 110 and a continuous aerosol flow synthesis reactor 510. The continuous aerosol flow synthesis reactor 510 may include a reaction tube 514. The reaction tube 514 may extend through one or a plurality of heating elements, such as a first furnace 520 and a second furnace 530, for example. Other heating elements, such as resistance heating elements and the like, are envisioned for heating sections of the reaction tube 514. A portion of the reaction tube 514 may be seasoned with a catalytically active precursor. As used in this disclosure, the term "season" refers to a process of pretreating the reaction tube 514 of aerosol flow synthesis reactor 510 with a catalytically active compound precursor vapor 136 (FIG. 6) to deposit a layer 516 of a catalytically active compound precursor on an inner surface 518 (FIG. 6) of the reaction tube 514. FIG. 6 illustrates a cross section of the reaction tube 514 having the layer 516 of catalytically active compound precursor deposited on the inner surface 518 of the reaction tube 514. Referring back to FIG. 5, in some embodiments, the reaction tube 514 may include at least a first heating zone 522 and a second heating zone 532, and the layer 516 of catalytically active compound precursor may be deposited on the inner surface 518 of the reaction tube 514 in the second heating zone 532 of the reaction tube 514.

Referring to FIGS. 5 and 6, in operation, the catalyst support precursor 104 and the diluent 106, plus any optional dopants, are combined and mixed in the vessel 102 to form the catalyst support precursor mixture 108. The catalyst support precursor mixture 108 is then passed to the continuous aerosol flow synthesis reactor 510. In the continuous aerosol flow synthesis reactor 510, the catalyst support precursor mixture 108 is aerosolized to form the aerosolized catalyst support precursor mixture 109, which comprises a plurality of droplets of the catalyst support precursor mixture 108 dispersed in a carrier gas 112. The carrier gas 112 entrains the droplets of the aerosolized catalyst support precursor mixture 109 and conveys the aerosolized catalyst support precursor mixture 109 through the reaction tube 514 of the continuous aerosol flow synthesis reactor 510. In the first heating zone 522, the reaction tube 514 is heated. The heat dries the diluent from the droplets of the aerosolized catalyst support precursor mixture 109, reacts the catalyst support precursors 104, or both to form the catalyst support particles 114. The catalyst support particles 114 are conveyed by the carrier gas 112 through the second heating zone 532. The second heating zone 532 is heated to cause the catalytically active compound precursor in the layer 516 of catalytically active compound precursor to vaporize to form the catalytically active compound precursor vapor 136 (FIG. 6). The catalytically active compound precursor vapor 136 distributes throughout the second heating zone 532 of the reaction tube 514. The catalyst support particles 114 carried by the carrier gas pass through the second heating zone 532 where the catalyst support particles 114 contact the catalytically active compound precursor vapor 136. The catalytically active compound precursor vapor 136 condenses on the surfaces of the catalyst support particles 114 to form the catalyst 101 comprising a layer of the catalytically active compound deposited on the catalyst support particles 114. The catalyst 101 may then be separated from the carrier gas 112 in the separator 140 downstream of the continuous aerosol flow synthesis reactor 210.

The method of producing the catalyst may include seasoning the reaction tube 514 extending through the second furnace with the catalytically active compound precursor. Seasoning the reaction tube 514 may comprise vaporizing the catalytically active compound precursor to form a catalytically active compound precursor vapor and condensing the catalytically active compound precursor vapor onto an inner surface 518 of the reaction tube 514 to form a layer 516 of the catalytically active compound precursor on the inner surface 518 of the reaction tube 514. The method may further include heating the reaction tube 514 to re-vaporize the catalytically active compound precursor from the inner surface 518 of the reaction tube 514 to produce the catalytically active compound precursor vapor 136, passing the plurality of catalyst support particles 114 through the reaction tube 514 where the plurality of catalyst support particles 114 contact the catalytically active compound precursor vapor 136, and condensing the catalytically active compound precursor vapor 136 on the surfaces of the catalyst support particles 114.

As previously discussed in relation to FIGS. 1-5, the catalysts 101 formed by the aerosol processing methods have individual atom molecules, clusters, or particles of the catalytically active compound deposited on the surfaces of the catalyst support particles 114. When deposited using the aerosol processing methods, this layer of catalytically active compounds is concentrated at the surfaces of the catalyst support particles 114 that are accessible to gaseous reactants rather than being fully or at least partially embedded in the catalyst support particles 114. Thus, the catalytically active compounds deposited on the surface of the catalyst support particles 114 are highly active compared to conventionally prepared catalysts. This enables the catalyst 101 formed using the aerosol processing methods to have less of the catalytically active compound but provide equivalent or increased catalytic activity relative to conventionally prepared catalysts, such as catalysts prepared by wet impregnation for example. In some embodiments, the catalyst 101 formed using the aerosol processing methods may have less than or equal to 50% of catalytically active compound compared to prepared catalysts having the catalytically active compound distributed throughout the catalyst support particle. In other embodiments, the catalyst 101 formed using the aerosol processing methods may have less than or equal to 25%, or less than or equal to 20%, or less than or equal to 15%, or less than or equal to 10% of the catalytically active compound compared to prepared catalysts having the catalytically active compound distributed throughout the catalyst support particle.

Reducing the amount of the catalytically active compounds in the catalyst 101 may reduce the cost of the catalyst 101, particularly when using costly catalytically active compounds such as platinum, gold, or palladium for example, relative to other prepared catalysts. Additionally, the aerosol processing method of forming the catalysts 101 enables continuous production of the catalysts. The aerosol processing system and methods described in this disclosure may enable greater control of the deposition rate and total amount of the catalytically active compound deposited on the surfaces of the catalyst support particles 114, which may enable control of the catalytic activity of the catalyst. The aerosol processing method may enable fine tuning of the catalytic activity of a catalyst for a specific application. Isomerization, metathesis, and metathesis and isomerization catalysts produced using the aerosol processing methods may result in less coke formation on the catalyst during metathesis reactions, which may lead to longer catalyst life.

In one example implementation, the aerosol process methods previously discussed may be used to synthesize an isomerization catalyst, metathesis catalyst, or a metathesis and isomerization catalyst for use in a process for producing olefins from a hydrocarbon feed stream, such as a metathesis process for producing propene from a hydrocarbon stream comprising butene. Conversion of 2-butene to propene via utilization of the metathesis and isomerization catalyst is described; however, it should be understood that this is merely for clarity and conciseness and other metathesis reactions are similarly envisioned.

A metathesis reaction is a chemical process involving the exchange of bonds between two reacting chemical species, which results in the creation of products with similar or identical bonding affiliations. This reaction is represented by the general scheme in the following reaction RXN1.

$$A\text{-}B + C\text{-}D \rightarrow A\text{-}D + C\text{-}B \quad \text{(RXN1)}$$

As shown in the following reactions RXN2 and RXN3, "isomerization" and "metathesis" of 2-butene to propene is generally a two-step process: 2-butene isomerization using an isomerization catalyst system and then cross-metathesis using a metathesis catalyst system. The 2-Butene Isomerization (reaction RXN2) may be achieved with both the silica and alumina support of the isomerization catalyst and the silica or silica and alumina support of the metathesis and isomerization catalyst. The Cross-Metathesis (RXN3) may be achieved by the oxometallate or metal oxide of the metathesis and isomerization catalyst or the metathesis catalyst. The metathesis and isomerization catalyst provides both the "isomerization" and "metathesis" steps with each component of the metathesis and isomerization catalyst providing individual functionalities.

Isomerization

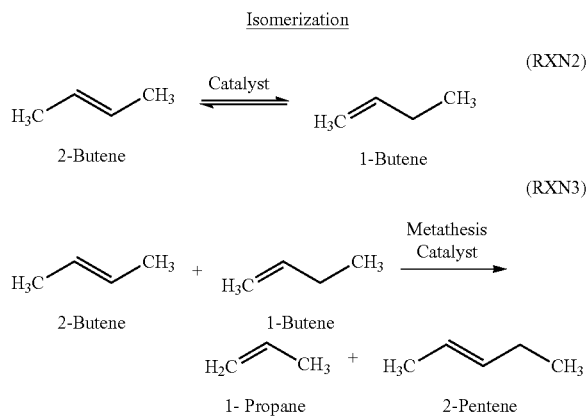

Referring to reactions RXN1 and RXN2, the "isomerization" and "metathesis" reaction is not limited to these reactants and products. However, reactions RXN2 and RXN3 provide a basic illustration of the reaction methodology. As shown in RXN3, the metathesis reaction takes place between two alkenes. The groups bonded to the carbon atoms of the double bond are exchanged between the molecules to produce two new alkenes with the exchanged groups. The specific catalyst that is selected for the olefin metathesis reaction may generally determine whether a cis-isomer or trans-isomer of the olefin reaction products is formed, as the coordination of the olefin molecules with the catalyst play an important role, as do the steric influences of the substituents on the double bond of the newly formed molecule.

Utilizing the aerosol processing system 100 and methods previously discussed in this disclosure for producing metathesis and isomerization catalysts, the metathesis catalysts, or isomerization catalysts may enable control of the properties and characteristics of the catalyst to customize the catalyst for the conversion of a variety of different compounds. Varying the parameters of the aerosol processing method may control formation of the resulting catalysts 101, such as metathesis and isomerization catalyst, metathesis catalyst, or isomerization catalyst for example, to exhibit a range of structural and chemical properties which may be customized or modified for different conversion reactions. For example, adjusting the structural and chemical properties of the catalyst support particles 114 may influence the isomerization functionality of the catalyst 101. Likewise, controlling the rate of condensation of the catalytically active compound precursor vapor 136 onto the catalyst support particles 114, the morphology of catalytically active compound deposited on the surface of the catalyst support particle 114, the amount of catalytically active compound deposited on the surface of the catalyst support particles 114, or both may enable control of the metathesis functionality of the catalyst 101.

The composition of the metathesis and isomerization catalyst, the metathesis catalyst, or the isomerization catalyst may be controlled by changing the catalyst support precursors 104, adding one or a plurality of dopants to the catalyst support precursors 104, modifying relative concentrations of the catalyst support precursors 104 in the catalyst support precursor mixture 108, and changing the type of carrier gas 112. For example, inclusion of a higher relative concentration of one catalyst support precursor, such as the silica precursor or alumina precursor, in the catalyst support precursor mixture 108 will result in a relatively higher concentration of the specific catalyst support precursor in the catalyst support particles 114.

Isomerization reactions may be affected by the acidity of the metathesis and isomerization catalyst or the isomerization catalyst. Acidity of the catalyst 101 may be controlled in at least two ways. First, the total number of acidic sites in the catalyst 101 may be controlled by changing the number of aluminum sites in the catalyst support particles 114. The number of aluminum sites may be controlled by modifying the proportion of the alumina precursor in the catalyst support precursor mixture 108 relative to the other precursors. Increasing the aluminum sites present in the catalyst support particles 114 increases the Al—OH that forms in the catalyst 101. The alumina incorporated into the catalyst 101 may allow for a balance between isomerization and propene yield. Without being bound by theory, it is believed the incorporation of too much alumina may form 1-butene (for example, from utilizing catalysts that include greater than 5 weight percent alumina), and the 1-butene formed may begin to react more commonly with itself forming ethylene and 3-hexene. To achieve the balance between isomerization and propene yield, the catalyst 101 may include from 1 weight percent to 5 weight percent alumnia based on the total weight of the catalyst support. In other embodiments, the catalyst 101 may comprise from 1 weight percent to 3 weight percent, from 1 weight percent to 2.5 weight percent, from 1.5 to 5 weight percent, from 1.5 weight percent to 3 weight percent, from 1.5 weight percent to 2.5 weight percent, from 2 weight percent to 5 weight percent, from 2 weight percent to 3 weight percent, from 2 weight percent to 2.5 weight percent, or from 3 weight percent to 5 weight percent alumina based on the total weight of the catalyst support.

In further embodiments, the catalyst 101 including from 1 weight percent to 5 weight percent alumina may be utilized to metathesize a stream of 2-butene at a reaction temperature of less than or equal to 550° C. In such embodiments, the propene yield may be about 12 mol %. In other embodiments the catalyst 101 may include from 1 weight percent to 5 weight percent alumina and be utilized to produce a propene yield of at least 15 mol. % or 20 mol % at a reaction temperature of less than or equal to 550° C.

Second, the acid strength of each of the aluminum sites is influenced by the environment around each of the aluminum sites and how the aluminum sites interact with the silica sites. The type of catalyst support precursors 104 may have an effect on the formation of aluminum sites. For example, fumed alumina has a large cluster of alumina already formed. Therefore, when fumed alumina is included as the alumina precursor in making silica-alumina based catalyst support particles, the interactions between the alumina and silica are largely predefined and limited to the interface of the two discrete regions of materials. Alternatively, in embodiments in which $Al(NO_3)_3$ is included as the alumina precursor, the aluminum sites created in the catalyst support particles 114 are generally single molecules fully surrounded by silica. Thus, each aluminum site can potentially interact with the silica in all dimensions.

In various embodiments, the metathesis and isomerization catalyst, the metathesis catalyst, or the isomerization catalyst formed by the aerosol processing methods may have a total acidity of less than or equal to 0.5 millimole/gram (mmol/g), or from 0.01 mmol/g to 0.5 mmol/g, from 0.1 mmol/g to 0.5 mmol/g, from 0.3 mmol/g to 0.5 mmol/g, or from 0.4 mmol/g to 0.5 mmol/g. It will be appreciated that in further embodiments the metathesis and isomerization catalyst, the metathesis catalyst, or the isomerization catalyst may have a total acidity that is less than 0.01 mmol/g or greater than 0.5 mmol/g. In embodiments, the acidity of the catalyst is sufficient to produce a desired selectivity of propene and reduced production of undesirable by-products such as aromatics. Increasing acidity may increase the overall butene conversion. However, this increased overall butene conversion may lead to less selectivity and increased production of by-products, such as aromatics for example, which can lead to catalyst coking and deactivation.

The particle size of the metathesis and isomerization catalyst, the metathesis catalyst, or the isomerization catalyst may be controlled by adjusting the concentration of the catalyst support precursor 104 in the catalyst support precursor mixture 108, the type and specification of aerosolizing unit 110, and the reactor configuration. For example, a higher concentration of the catalyst support precursors 104 in the catalyst support precursor mixture 108 relative to water or other diluent 106 results in larger catalyst support particles 114 as less water or other diluent is available to vaporize from each aerosolized droplet. Additionally, different aerosolizing units 110 may produce different size droplets of the aerosolized catalyst support precursor mixture 109 during aerosolization, thus, producing different particle sizes of the catalyst support particles 114. For example, changing the frequency in an ultrasonic nebulizer changes the droplet size of the aerosolized catalyst support precursor mixture 109 generated by the ultrasonic nebulizer. Changing the droplet size changes the particle size of the catalyst support particles 114. Increasing turbulent flow within the aerosolizing unit 110, the first heating zone 120, or both may also increase particle size by causing droplets to collide and coalesce together. Similarly, impactors positioned within the aerosolizing unit 110 or before the first heating zone 120, or both may separate larger wet droplets of the aerosolized catalyst support precursor mixture 109 and permit only smaller droplets to enter and pass through the first heating zone 120. This results in reducing the average size of the catalyst support particles 114. In some embodiments, the catalyst support particles 114 may have a particle size of from 50 nanometers (nm) to 50 microns (μm). In embodiments in which the catalytically active compound precursor forms into clusters or particles that are then deposited on the surfaces of the catalyst support particles 114, the particle size of the catalytically active compound clusters or particles may be less than or equal to 20 nm.

The surface area of the catalyst may be controlled by adjusting the type and amount of the catalyst support precursors 104, including inert constituents, sacrificial constituents, or both, in the catalyst support precursor mixture 108. Inert and sacrificial constituents may include polystyrene latex for example. When heated to high temperatures, the polystyrene latex burns off, leaving pores where the polystyrene latex was previously. One having skill in the art will appreciate that other sacrificial continuants may be utilized which burn off at an elevated temperature to produce a catalyst having an increased surface area caused by removal of the inert and sacrificial constituents from the catalyst. Further, selection of fumed silica and fumed alumina as catalyst support precursors 104 may result in an increased surface area. When aerosolized, the high fractal surface areas of fumed silica and fumed alumina structures are generally preserved. This high fractal surface area results in an increased surface area when compared to non-fumed precursors which result in more spherical, dense particles, with lower surface area since they do not have much internal surface area. The surface area may also be controlled by adjusting the configuration of the aerosol processing system 100. In some embodiments, the catalyst 101 formed by the aerosol processing methods may have a surface area of from 100 meters squared per gram ($m^2/g$) to 700 $m^2/g$. In other embodiments, the catalyst may have a surface area of from 450 $m^2/g$ to 600 $m^2/g$, from 250 $m^2/g$ to 350 $m^2/g$, from 275 $m^2/g$ to 325 $m^2/g$, or from 275 $m^2/g$ to 300 $m^2/g$.

The crystallinity of the catalyst support particles 114 may be controlled by adjusting the type and amount of the catalyst support precursors 104, the temperature of the first heating zone 120, the residence time in the first heating zone 120, and the cooling rate of the catalyst 101. For example, the use of a metal oxide or oxometallate that contains a single metal center versus multiple metal centers as a catalyst support precursor 104 can lead to more dispersion because the fracturing of the cluster is not required. The more metal centers of the metal oxide or oxometallate source that it contains the more fracturing that is required to form crystallinity. Regarding cooling rate, a relatively slower cooling rate provides additional time for the crystal arrangement to occur, where a relatively faster cooling rate can lock atoms into metastable or amorphous states. Regarding temperature and residence time in the first heating zone 120, increasing the temperature, residence time, or both may cause metal oxides or oxometallates to migrate on the surface of the catalyst support particles 114 which may increase crystallite size.

In some embodiments, the catalyst support particles 114 may have a pore size distribution of from 2.5 nanometers (nm) to 40 nm and a total pore volume of at least 0.600 cubic centimeters per gram (cm³/g). Without being bound by theory, the pore size distribution and pore volume are sized to achieve better catalytic activity and reduced blocking of pores by metal oxides, whereas smaller pore volume and pore size catalyst systems are susceptible to pore blocking and thereby reduced catalytic activity. In some embodiments, the catalyst support particles 114 may have a pore size distribution of from 2.5 nm to 40 nm, from 2.5 nm to 20 nm, from 2.5 nm to 4.5 nm, from 2.5 nm to 3.5 nm, from 8 nm to 18 nm, or from 12 nm to 18 nm. In some embodiments, the catalyst may have a total pore volume of from 0.600 cm³/g to 2.5 cm³/g, from 0.600 cm³/g to 1.5 cm³/g, from 0.600 cm³/g to 1.3 cm³/g, from 0.600 cm³/g to 0.800 cm³/g, from 0.600 cm³/g to 0.700 cm³/g, or from 0.900 cm³/g to 1.3 cm³/g.

Dispersed Tungsten Catalysts

According to one or more embodiments, tungsten may be dispersed throughout the alumina and silica material. In such embodiments, the tungsten may be applied along with the alumina and silica during the aerosol processing, referred to as an "aerosolized" or "aerosol-produced" catalyst herein. This is different than tungsten applied by wet impregnation, as is described herein. In one or more embodiments, the amount of tungsten may be reduced to, for example, less than 5 weight percent. While it would be expected that reduced tungsten loading would decrease catalytic activity, it has been observed that the presently disclosed catalysts, even with reduced tungsten loading, have improved performance when a particular amount of alumina is incorporated into the catalyst. Such alumina content may cause increased single site tungsten oxide, promoting catalytic activity. Even at tungsten loading of less than 5 weight percent, acceptable catalytic activity was achieved by the incorporation of alumina. For example, the weight ratio of alumina to silica may be from 0.01:99.9 to 5:95 (such as from 0.1:99.9 to 1:99, from 1:99 to 2:98, from 2:98 to 3:97, from 3:97 to 4:96, from 4:96 to 5:95, or combinations thereof). In such embodiments, the combination of alumina and silica may constitute at least 90 weight percent of the catalyst, or even at least 95 weight percent of the catalyst.

One or more embodiments of the present disclosure are directed to methods of synthesizing metathesis and isomerization catalysts, metathesis catalysts, and isomerization catalysts. Specifically, the present embodiments are related to synthesizing a metathesis and isomerization catalyst, an isomerization catalyst, or a metathesis catalyst via an aerosolization process.

Synthesizing a metathesis and isomerization catalyst, a metathesis catalyst, or an isomerization catalyst in accordance with at least one embodiment of this disclosure includes forming a catalyst precursor mixture, aerosolizing the catalyst precursor mixture, drying the aerosolized catalyst precursor mixture to form a dried catalyst precursor, and reacting the dried catalyst precursor to yield the metathesis and isomerization catalyst, the metathesis catalyst, or the isomerization catalyst.

The metathesis and isomerization catalyst or metathesis catalyst comprises a silica and alumina support with an oxometallate or metal oxide distributed within the silica and alumina support. The silica and alumina support as well as the oxometallate or metal oxide distributed within the silica and alumina support participate in the isomerization of 2-butene. The oxometallate or metal oxide distributed within the silica and alumina support is responsible for the metathesis portion of the reaction. Both functionalities can be controlled independently for a variety of desired reactions through the use of various metal precursors forming the oxometallate or metal oxide distributed within the silica and alumina support and dopants in the catalyst precursor mixture.

The catalyst precursor mixture comprises a catalyst precursor and a diluent. In one or more embodiments, the catalyst precursor comprises an oxometallate precursor and at least one of an alumina precursor and a silica precursor. In further embodiments, the catalyst precursor comprises a metal oxide precursor and at least one of an alumina precursor and a silica precursor.

Throughout this disclosure reference is made to the metathesis and isomerization catalyst; however it should be understood that this is merely for conciseness and a metathesis catalyst alone or an isomerization catalyst alone may be generated in accordance with the methods of this disclosure. Specifically, omitting the oxometallate and metal oxide precursor from the catalyst precursor mixture results in the isomerization catalyst alone. Similarly, adjusting the chemistry of the silica precursor and the alumina precursor results in a silica-alumina support for the oxometallate or metal oxide without an isomerization functionality to generate the metathesis catalyst alone.

In one or more embodiments the silica precursor comprises fumed silica. In various other embodiments, the silica precursor comprises colloidal silica, silane ($SiH_4$), silicon tetrachloride, or tetraethyl orthosilicate (TEOS).

In one or more embodiments the alumina precursor comprises aluminum nitrate ($Al(NO_3)_3$). In various other embodiments, the alumina precursor comprises fumed alumina or additional aluminum salts and their hydrates, such as $AlCl_3$, $AlPO_4$, or $Al_2(SO_4)_3$.

In various embodiments, the oxometallate precursor comprises a tungstate precursor. In one or more embodiments the tungstate precursor comprises ammonium metatungstate $((NH_4)_6H_2W_{12}O_{40})$. In various other embodiments, the tungstate precursor comprises tungstic acid, phosphotungstic acid, or sodium tungstate.

In various embodiments the metal oxide precursor comprises a precursor of one or more oxides of a metal from the Groups 6-10 of the IUPAC Periodic Table. In one or more embodiments, the metal oxide may be an oxide of rhenium, tungsten, cerium, or combinations thereof. In a specific embodiment, the metal oxide is tungsten oxide ($WO_3$). It should be understood that where a material comprises tungsten, tungsten oxide is contemplated as an embodiment which comprises tungsten.

In various embodiments, the diluent is water or an organic solvent. Example organic solvents include methanol, ethanol, acetone, or a combination of solvents. In embodiments with water as the diluent, an aqueous catalyst precursor mixture is formed.

In embodiments the catalyst precursor solution is absent a surfactant. Without wishing to be bound by theory, the catalyst precursor mixture forms the metathesis and isomerization catalyst without the support and assistance of a surfactant.

In one or more embodiments the catalyst precursor comprises 0.1 to 99.9 weight % (weight percent) silica precursor, 0.1 to 5 weight percent oxometallate precursor or metal oxide precursor, and 0.1 to 5 weight percent alumina precursor.

The catalyst precursor mixture may be formed as a solution or as a suspension. For example, with fumed precursors or colloidal precursors, a suspension is formed for the catalyst precursor mixture. However, for precursors comprising metal salts, a solution is formed.

The catalyst precursor mixture is aerosolized to form an aerosolized mixture of the catalyst precursor mixture. In one or more embodiments the catalyst precursor mixture is aerosolized in a nebulizing unit. A variety of nebulizing units are envisioned, as long as they generate a liquid spray. Examples of nebulizing units include ultrasonic transducers and spray nozzles. One non-limiting benefit of an ultrasonic transducer is that it is readily scalable and highly controllable.

Aerosol processing overcomes deficiencies in previous methods of forming a metathesis catalyst. Specifically, using a wet impregnation or grafting technique to infuse a metal oxide into a support structure has inherent limitations. The support materials must be synthesized in a separate step with infusion of a metal oxide or other desired species requiring secondary processing. Further, accessibility of the entire particle volume is not always possible with a wet impregnation or grafting technique. Conversely, with aerosol processing, the metal oxide or other desired species is entrained during initial processing and is naturally able to be diffused throughout the entire particle volume or to be strategically concentrated on the surface of the particle.

Prior to aerosolizing the catalyst precursor, the catalyst precursor is combined with the diluent to form the catalyst precursor mixture. In one or more embodiments, the catalyst precursor mixture is aerosolized at a catalyst precursor concentration of between 1 weight percent and 20 weight percent. In various further embodiments, the catalyst precursor is combined with water and aerosolized at a catalyst precursor concentration of between 1 weight percent and 6 weight percent, between 2 weight percent and 5 weight percent, or between 2 weight percent and 4 weight percent.

In one or more embodiments, a carrier gas may transport the aerosolized catalyst precursor mixture into a heated furnace for drying of the aerosolized catalyst precursor. In one or more embodiments, the carrier gas is air. In various additional embodiments, the carrier gas comprises nitrogen, argon, helium, or mixtures of multiple gases. In yet further embodiments, the carrier gas may be a reactant for the formation of the metathesis and isomerization catalyst, the metathesis catalyst, or the isomerization catalyst. For example, the carrier gas may be silane ($SiH_4$). The selection of a non-reactive gas or a reactive gas is dependent upon the precursors utilized and the desired metathesis and isomerization catalyst, metathesis catalyst, or isomerization catalyst to be formed.

The heated furnace dries the aerosolized catalyst precursor mixture and also has the potential to initiate formation of crystallinity within the metathesis and isomerization catalyst, metathesis catalyst, or isomerization catalyst formed from the dried aerosolized catalyst precursor. It is noted that the aerosolized catalyst precursor mixture need not be fully dried prior to initiation of crystallization. As illustrated in FIG. 1, droplets of the aerosolized catalyst precursor mixture start to dry and the catalyst precursor becomes more concentrated. Subsequently, during heating, the dried or partially dried catalyst precursor can react to form amorphous structures, crystalline structures, or a combination of amorphous and crystalline structures depending upon the catalyst precursor chemistry. In one or more embodiments the furnace is heated to between 500° C. and 1500° C. In further embodiments the furnace is heated to between 1000° C. and 1500° C. The elevated temperature results in the catalyst precursors reacting to form the desired products. In further embodiments, to merely dry the catalyst precursor mixture, the furnace is heated to between 100° C. and 800° C.

In one or more embodiments, the heated furnace comprises multiple temperature zones. The different temperature zones may operate at different temperatures. For example, a first temperature zone between 100° C. and 500° C. may be utilized to dry or partially dry the aerosolized catalyst precursor mixture, and a second temperature zone between 800° C. and 1500° C. may be utilized to react the catalyst precursors and form the desired products.

In one or more embodiments, the residence time in the heated furnace is between 0.1 and 10 seconds. If the residence time is of insufficient length the particles do not dry and may be left unreacted such that the final desired metathesis and isomerization catalyst, the final metathesis catalyst, or the final isomerization catalyst are not formed. Conversely, if the residence time is unnecessarily extended energy is wasted and the metathesis and isomerization catalyst particles, metathesis catalyst particles, or isomerization catalyst particles may be lost to the heated furnace tube walls. Additionally, too rapidly drying the aerosolized catalyst precursor mixture can lead to particle shells which can collapse with further processing opposed to solid catalyst particles.

The crystallinity of the metal oxide in the formed metathesis and isomerization catalyst or metathesis catalyst is dependent upon various factors including the oxometallate or metal oxide loading in the silica and alumina support. At low oxometallate or metal oxide loadings, such as 2-5 weight percent, there is no observable formation of crystallinity in the heated furnace. Post treatment of the metathesis and isomerization catalyst or metathesis catalyst collected from the heated furnace in air, such as calcination at 550° C., increases the overall crystallinity of the oxometallate or metal oxide.

Previous attempts at using a spray dryer for aerosol processing have been met with several limitations. Specifically, the temperature range for processing was limited to between the freezing point of the solution for processing and 220° C. Further, a conventional spray dryer setup is limited to two solutions being mixed at the reactor.

The feed rate of catalyst precursor into the heated furnace varies based on the flow rate of carrier gas. In general, the faster the flow rate of the carrier gas, the higher the feed rate of catalyst precursor into the heated furnace. However, the carrier gas flow rate also can impact residence time, with a higher carrier gas flow rate resulting in a reduced residence time. A balance must be reached to maximize production of metathesis and isomerization catalyst, metathesis catalyst, or isomerization catalyst through an increased flow rate of catalyst precursor without overly reducing the residence time in the heated furnace. In an ultrasonic transducer system, a carrier gas flow rate of 1.25 L/min/transducer to 3.75 L/min/transducer is a desirable range.

In one or more embodiments the method further comprises collecting the metathesis and isomerization catalyst, metathesis catalyst, or isomerization catalyst with a filter from the flow of the carrier gas exiting the heated furnace. An example filter comprises borosilicate fibers bound with polyvinylidene fluoride (PVDF) configured to have a 93% efficiency at capturing 0.01 µm particles. The filter may also be comprised of any typically commercially available bag house filter material. In selecting a filter there is a desire to balance pore size of the filter to sufficiently collect the catalyst particles with the resulting pressure increase which results as the filter collects catalyst particles. As the filter begins to clog and a particle cake forms, the filter becomes a more efficient filter and the pressure starts to rise. In operation, the resulting pressure rise may be used as an indicator of the quantity of metathesis and isomerization catalyst, metathesis catalyst, or isomerization catalyst collected within the filter.

As the water or other diluent is removed from the individual droplets of the aerosolized catalyst precursor solution the droplets become more concentrated.

In one or more embodiments the catalyst precursor comprises one or more dopants. Envisioned dopants include, but are not limited to, titania, rhenia, and phosphates. Synthesis of metathesis and isomerization catalysts, metathesis catalysts, or isomerization catalysts via an aerosolization scheme allows for the inclusion of dopants during initial processing and formation of the metathesis and isomerization catalyst, metathesis catalyst, or isomerization catalyst opposed to relying on post-processing addition. The dopant may be included as a constituent of the catalyst precursor solution and thus is entrained in-situ during aerosolization and standard formation of the metathesis and isomerization catalyst, the metathesis catalyst, or the isomerization catalyst.

In further embodiments, the method of synthesizing the metathesis and isomerization catalyst, the metathesis catalyst, or the isomerization catalyst may comprise aerosolizing a dopant stream concurrently with aerosolizing the catalyst precursor to yield the metathesis and isomerization catalyst, the metathesis catalyst, or the isomerization catalyst with dopants entrained in the silica and alumina support. In further embodiments, the dopant stream may be added after a first heated furnace and before a second heated furnace.

Control of the characteristics of the metathesis and isomerization catalyst, the metathesis catalyst, or the isomerization catalyst allows for the conversion of a variety of different chemicals. Varying the synthesis characteristics of the aerosolization process may allow the resulting metathesis and isomerization catalyst, metathesis catalyst, or isomerization catalyst to exhibit a range of structural and chemical properties which are optimized for differing conversion reactions. For example, adjusting the structural and chemical properties of the silica and alumina support may allow the isomerization functionality to be optimized and adjusting the properties of the oxometallate or metal oxide distributed within the silica and alumina support may allow the metathesis functionality to be optimized.

The composition of the metathesis and isomerization catalyst, the metathesis catalyst, or the isomerization catalyst may be controlled by changing the precursors, the selection and incorporation of carrier gas, and the relative concentrations of the precursors and carrier gas in the catalyst precursor solution. For example, inclusion of a higher relative concentration of one precursor in the catalyst precursor solution will result in a relatively higher concentration in the final metathesis and isomerization catalyst, the final metathesis catalyst, or the final isomerization catalyst. Additionally, oxometallates and metal oxides in the metathesis and isomerization catalyst or metathesis catalyst in accordance with the present disclosure may be generated using air as the carrier gas. Specifically, air comprises oxygen which can be incorporated into the resulting metathesis and isomerization catalyst or metathesis catalyst. Further, in embodiments with water as a diluent, oxygen from the heated water may also be used as an oxygen source.

The acidity of the metathesis and isomerization catalyst, the metathesis catalyst, or the isomerization catalyst may be controlled with the amount and selection of the alumina precursor in the catalyst precursor solution. Isomerization is affected by the acidity of the metathesis and isomerization catalyst or the isomerization catalyst. Acidity is controlled in at least two ways. First, the total number of acidic sites in the metathesis and isomerization catalyst or the isomerization catalyst is controlled by the amount of aluminum incorporated into the structure. The more aluminum sites that are present the more Al—OH will be present. Second, the acid strength is also affected by the aluminum sites and how they interact with the silica sites. The choice of catalyst precursors may have an effect on the formation of various sites. For example: fumed alumina has a large cluster of alumina already formed, therefore the interactions between the alumina and silica are largely predefined and limited to the interface of the two discrete materials. In the case of $Al(NO_3)_3$ the alumina that is created is a single molecule and can potentially interact with silica in all dimensions remaining isolated. Further, in various embodiments, the metathesis and isomerization catalyst, the metathesis catalyst, or the isomerization catalyst may have a total acidity of up to about 0.5 millimole/gram (mmol/g), or about 0.01 mmol/g to about 0.5 mmol/g, or about 0.1 mmol/g to about 0.5 mmol/g, or about 0.3 mmol/g to about 0.5 mmol/g, or about 0.4 mmol/g to about 0.5 mmol/g. It will be appreciated that in further embodiments the metathesis and isomerization catalyst, the metathesis catalyst, or the isomerization catalyst may have a total acidity below 0.01 mmol/g or above 0.5 mmol/g. Acidity of the catalyst is selected to yield the desired selectivity of propylene and reduced production of undesirable by-products such as aromatics. Increasing acidity may increase the overall butene conversion; however, this increased conversion may lead to less selectivity and increased production of aromatic by-products, which can lead to catalyst coking and deactivation.

The particle size of the metathesis and isomerization catalyst, the metathesis catalyst, or the isomerization catalyst may be controlled by adjusting the precursor concentration in the aerosolized catalyst precursor solution, the aerosolization method and specifications, and the reactor configuration. For example, a higher concentration of precursors relative to water or other diluent in the catalyst precursor solution results in larger particles as less water or other diluent is available to evaporate from each aerosolized droplet. Additionally, different aerosolization methods result in differing size droplets and thus differing particle sizes of the final metathesis and isomerization catalyst, the final metathesis catalyst, or the final isomerization catalyst. Changing the frequency in an ultrasonic nebulizer can impact the particle size of the metathesis and isomerization catalyst, the metathesis catalyst, or the isomerization catalyst as the droplet size of the catalyst precursor mixture will change at different frequencies. Increasing turbulent flow within the aerosolization unit or heated furnace can increase particle size as droplets collide and merge together. Similarly, impactors can separate larger wet droplets of the catalyst precursor mixture and only allow smaller droplets to enter the heated furnace resulting in smaller catalyst particle sizes. Furthermore, in various embodiments, the metathesis and isomerization catalyst, the metathesis catalyst, or the isomerization catalyst may have a particle size of from about 5 nm to about 4000 nm, or about 100 nm to about 2500 nm. In additional embodiments, the metathesis and isomerization catalyst, the metathesis catalyst, or the isomerization catalyst may be an aggregate comprised of primary particles with sizes of about 5 nm to 250 nm. These metathesis and isomerization catalysts, metathesis catalysts, or isomerization catalysts may be further granulated to 1 μm to about 100 μm, or about 10 μm to about 40 μm.

The surface area of the metathesis and isomerization catalyst, the metathesis catalyst, or the isomerization catalyst may be controlled by adjusting precursors, including inert and sacrificial constituents in the catalyst precursor solution, and adjusting the reactor configuration. Inert and sacrificial constituents may include polystyrene latex or NaCl, for example. When heated to high temperature, the polystyrene latex burns off, leaving pores where the polystyrene latex was previously. Similarly, with NaCl, once the metathesis and isomerization catalyst particle, the metathesis catalyst particle, or the isomerization catalyst particle is formed it may be placed in water and the NaCl dissolved away, leaving behind the non-NaCl particle structure. One having skill in the art will appreciate that other sacrificial continuants may be utilized which burn off at an elevated temperature or which are soluble in water or other solvent to result in a metathesis and isomerization catalyst, metathesis catalyst, or isomerization catalyst with the sacrificial constituent removed and an increased surface area. Further, selection of fumed silica and fumed alumina as precursors may result in an increased surface area. When aerosolized, the high fractal surface area of fumed silica and fumed alumina structures is generally preserved. This high fractal surface area results in an increased surface area when compared to non-fumed precursors which result in more spherical, dense particles, with lower surface area since they do not have much internal surface area. Moreover, while broader ranges are contemplated, the metathesis and isomerization catalyst, the metathesis catalyst, or the isomerization catalyst may, in one or more embodiments, include a surface area of about 100 meters/gram ($m^2/g$) to about 700 $m^2/g$. In further embodiments, the metathesis and isomerization catalyst, the metathesis catalyst, or the isomerization catalyst may have a surface area of from about 450 $m^2/g$ to about 600 $m^2/g$, or about 250 $m^2/g$ to about 350 $m^2/g$, or about 275 $m^2/g$ to about 325 $m^2/g$, or about 275 $m^2/g$ to about 300 $m^2/g$.

The crystallinity of the metathesis and isomerization catalyst, the metathesis catalyst, or the isomerization catalyst may be controlled by adjusting the precursor selection, the heated furnace temperature, the furnace residence time, and the cooling rates of the metathesis and isomerization catalyst, the metathesis catalyst, or the isomerization catalyst. For example, a relatively slower cooling rate provides additional time for the crystal arrangement to occur, where a relatively faster cooling rate can lock atoms into metastable or amorphous states, which are not typically found at equilibrium. Regarding precursor selection, the use of a metal oxide or oxometallate source that contains a single metal center versus multiple metal centers can lead to more dispersion because the fracturing of the cluster is not required. The more metal centers the metal oxide or oxometallate source that contains the more fracturing that is required to form crystallinity. Regarding furnace temperature and residence time, at elevated temperatures or elongated times the metal oxides or oxometallates may migrate on the surface which allows for increased crystallite size.

Moreover, the pore size distribution of the metathesis and isomerization catalyst, the metathesis catalyst, or the isomerization catalyst in one or more embodiments range from about 2.5 nm to about 40 nm and a total pore volume of at least about 0.600 $cm^3/g$. Without being bound by theory, the present pore size distribution and pore volume are sized to achieve better catalytic activity and reduced blocking of pores by metal oxides, whereas smaller pore volume and pore size catalyst systems are susceptible to pore blocking and thereby reduced catalytic activity.

In one or more embodiments, the pore size distribution of the metathesis and isomerization catalyst, the metathesis catalyst, or the isomerization catalyst may range from about 2.5 nm to about 40 nm, or about 2.5 nm to about 20 nm, or about 2.5 nm to about 4.5 nm, or about 2.5 nm to about 3.5 nm, or about 8 nm to about 18 nm, or about 12 nm to about 18 nm. In further embodiments, the total pore volume may be from about 0.600 $cm^3/g$ to about 2.5 $cm^3/g$, or about 0.600 $cm^3/g$ to about 1.5 $cm^3/g$, or about 0.600 $cm^3/g$ to about 1.3 $cm^3/g$, or about 0.600 $cm^3/g$ to about 0.800 $cm^3/g$, or about 0.600 $cm^3/g$ to about 0.700 $cm^3/g$, or about 0.900 $cm^3/g$ to about 1.3 $cm^3/g$.

EXAMPLES

The following examples illustrate the preparation of various metathesis and isomerization catalysts based on the methods disclosed herein.

Example 1

Preparation of Catalysts with Tungsten Evaporated Coating

To produce each catalyst sample of Example 1 (Sample 1, Sample 2, Sample 3, and Sample 4), a catalyst support precursor mixture was first prepared by combining fumed silica, aluminum nitrate, and water. The fumed silica used was AEROSIL® 380 fumed silica obtained from Evonik Industries. The weight percent of each material in the fabricated catalyst prior to tungsten application are shown in Table 2.

TABLE 2

|  | Weight percent Silica | Weight percent Alumina |
| --- | --- | --- |
| Sample 1 | 100 | 0 |
| Sample 2 | 99 | 1 |
| Sample 3 | 98 | 2 |
| Sample 4 | 95 | 5 |

The catalyst support precursor mixture for each sample was sonicated for 20 minutes. The catalyst support precursor mixture was then aerosolized into a fine mist of micrometer sized droplets using an ultrasonic transducer.

The aerosolized catalyst support precursor mixture was then passed to an aerosol processing system that included a first furnace and a second furnace in series with and downstream of the first furnace.

The first furnace (first heating zone) was configured to form agglomerated, spherical particles of fumed silica from the aerosolized catalyst support precursor mixture. The first furnace included a heated length of 12 inches and was maintained at a temperature of 600° C.

The second furnace had an overall length of 12 inches, and a heated length of 6 inches, which included the distance of 3 inches from the inlet of the second furnace to a distance of 9 inches from the inlet of the second furnace. The temperature of the second furnace was 1250° C.

An alumina crucible containing an initial mass of tungsten oxide ($WO_3$) was positioned in the second furnace. The tungsten oxide used was >99% tungsten oxide (lot no. A0348621) obtained from Acros Organics. The second furnace was independently heated to 1250° C. to control the evaporation rate of the tungsten oxide. The weight of $WO_3$ in the crucible was measured before and after each experiment to determine the amount of $WO_3$ vaporized into the second furnace.

The aerosolized catalyst support precursor mixture was conveyed by a carrier gas through the first furnace and the second furnace at a carrier gas flow rate of 10 liters per minute (L/min) to produce each catalyst of Samples 1-4. The carrier gas was particle-free, oil-free air. Each catalyst of Samples 1-4 were collected on a filter. The amount of $WO_3$ deposited on the synthesized metathesis catalyst was determined by Scanning Electron Microscope and Energy Dispersive Spectroscopy (SEM/EDS) and inductively coupled plasma atomic emission spectroscopy (ICP-AES) so that each of Samples 1-4 contained 2.5 weight percent tungsten based on the total weight of the catalyst sample.

Example 2

Catalytic Characterization of Catalysts of Example 1

To evaluate the effect of varying alumina content on metathesis and isomerization, Samples 1-4 were utilized to synthesize propene from a stream of 2-butene and nitrogen in a fixed bed reactor operated at 450° C. Each catalyst was tested sequentially to provide performance data for each catalyst.

The fixed-bed flow reactor system had a quartz tube with a bed of catalyst disposed between layers of quartz wool. Samples 1-4 were each serially mounted in the quartz tube as the bed of catalyst disposed between the layers of quartz wool. Each sample was first activated at a temperature of 450° C. under nitrogen flow at 0.015 liters/minute (L/min) for 1 hour. At the desired reaction temperature (450° C.), a feed stream comprising a 50/50 mixture of cis-2 butene and trans-2-butene was introduced into the reactor to start the reaction. The reaction was performed at 450° C. and at a gas hourly space velocity of 2700 per hour ($h^{-1}$), using nitrogen as a diluent. The feed stream had 10 weight percent of a 50/50 by weight mixture of cis-2-butene and trans-2-butene based on the total mass flow rate of the feed stream. The flow stream exiting the fixed bed flow reactor was passed to a gas chromatograph for analysis of the product stream. The propene selectivity for each of Samples 1-4 is provided subsequently in Table 3. Table 3 also provides the silica and alumina content of the catalyst, based on the total weight of the support and the tungsten content, based on the total weight of the catalyst.

porating alumina into catalyst support materials at various concentrations during a high temperature aerosol process, catalysts are generated that exhibit high activity per $WO_3$ site for the conversion of 2-butene to propene. Additionally, Samples 2-4 generally resulted in greater 2-butene conversion and propene yield than Sample 1, which had 100 weight percent silica.

Example 3

Preparation of Dispersed Tungsten Aerosolized Catalysts

Catalysts of Example 3 (Sample 5, Sample 6, and Sample were prepared by aerosol methods where tungsten was aerosolized with the alumina and silica. To produce Sample 5, a catalyst support precursor mixture was prepared from 12.0 g. fumed silica, 0.329 g. ammonium metatungstate, and 570 ml water. The precursor was provided to an ultrasonic nebulizer at 21 ml/min unit aerosol flow was observed. Subsequently, the flow of precursor to the ultrasonic nebulizer was reduced to 1 ml/min for 120 min. The aerosolized precursor was transferred to a heated furnace at 1000° C. with a flow of air at 5 L/min. Flow of air was continued for 120 min. Upon exit from the heated furnace, the formed metathesis and isomerization catalyst was collected in a filter. A total of 221 mg of metathesis and isomerization catalyst was collected.

To produce Sample 6, a catalyst support precursor mixture was prepared from 12.0 g. fumed silica, 22.2 g. aluminum nitrate, 0.329 g. ammonium metatungstate, and 570 ml water. The precursor was provided to an ultrasonic nebulizer at 21 ml/min unit aerosol flow was observed. Subsequently, the flow of precursor to the ultrasonic nebulizer was reduced to 1 ml/min for 120 min. The aerosolized precursor was transferred to a heated furnace at 1000° C. with a flow of air at 5 L/min. Flow of air was continued for 120 min. Upon exit from the heated furnace, the formed metathesis and isomerization catalyst was collected in a filter. A total of 221 mg of metathesis and isomerization catalyst was collected.

To produce Sample 7, a catalyst support precursor mixture was prepared from 12.0 g. fumed silica, 22.2 g. aluminum nitrate, 0.329 g. ammonium metatungstate, and 570 ml water. The precursor was provided to an ultrasonic nebulizer at 21 ml/min unit aerosol flow was observed. Subsequently, the flow of precursor to the ultrasonic nebulizer was reduced to 1 ml/min for 120 min. The aerosolized precursor was

TABLE 3

Effect of alumina content on metathesis and isomerization.

| | Preparation Method | Tungsten content | Silica content | Alumina content | Conversion 2-butene (mol %) | Propene yield (mol %) |
|---|---|---|---|---|---|---|
| Sample 1 | Aerosol Vapor Coating | 3.52 weight percent | 100 weight percent | 0 weight percent | 31.02% | 2.19% |
| Sample 2 | Aerosol Vapor Coating | 2.71 weight percent | 99 weight percent | 1 weight percent | 64.23% | 15.26% |
| Sample 3 | Aerosol Vapor Coating | 3.12 weight percent | 98 weight percent | 2 weight percent | 72.66% | 20.69% |
| Sample 4 | Aerosol Vapor Coating | 4.47 weight percent | 95 weight percent | 5 weight percent | 55.74% | 13.52% |

As shown in Table 3, Sample 3 having 2 weight percent alumina produced results with the greatest 2-butene conversion and propene yield. These results show that by incortransferred to a heated furnace at 1000° C. with a flow of air at 5 L/min. Flow of air was continued for 120 min. Upon exit from the heated furnace, the formed metathesis and isomerization catalyst was collected in a filter. A total of 221 mg of metathesis and isomerization catalyst was collected.

Comparative Example A

Synthesis of Comparative Catalyst by Wet Impregnation Methods

Catalysts of Comparative A (Samples A1 and Sample A2) were prepared by wet impregnating $WO_3$ onto a silica support. The silica support was CARiACT Q-10 silica catalyst support obtained from Fuji Silysia Chemical. The silica catalyst support was wet impregnated with a solution of ammonium metatungstate hydrate to produce the catalysts of Comparative Sample A1 having 2.5 weight percent and Sample A2 having 10 weight percent $WO_3$, based on the total weight of the catalyst.

Example 4

Catalytic Characterization of the Catalysts of Example 3 and Comparative Example A To evaluate the effect of varying alumina content on metathesis and isomerization, the catalysts of Example 3 and Comparative Example A were compared. Each catalyst was tested sequentially to provide performance data for each catalyst.

The fixed-bed flow reactor system had a quartz tube with a bed of catalyst disposed between layers of quartz wool. The samples were each serially mounted in the quartz tube as the bed of catalyst disposed between the layers of quartz wool. Each catalyst was first activated at a temperature of 450° C. under nitrogen flow at 0.015 liters/minute (L/min) for 1 hour. At the desired reaction temperature (450° C.), a feed stream comprising of a 50/50 mix of cis-2 butene and trans-2-butene was introduced into the reactor to start the reaction. The reaction was performed at 450° C. and at a gas hourly space velocity of 2700 per hour ($h^{-1}$), using nitrogen as a diluent. The feed stream had 10 weight percent of a 50/50 mix of cis-2 butene and trans-2-butene based on the total mass flow rate of the feed stream. The flow stream exiting the fixed bed flow reactor was passed to a gas chromatograph for analysis of the product stream. The percentage of propene selectivity for the tested samples are provided subsequently in Table 4. Table 4 also provides the silica and alumina content of the catalyst, based on the total weight of the support and the tungsten content, based on the total weight of the catalyst.

As shown in Table 4, the aerosol synthesized catalysts of Samples 1-4 (see Table 3) generally resulted in greater 2-butene conversion and propene yield than the tungsten aerosolized or wet impregnated catalysts of the samples of Table 4 at reaction temperatures below 550° C., more specifically at temperatures of 450° C. With the combination of lower temperatures and lack of any crystalline $WO_3$ in the catalyst material, there is very little isomerization of 2-butene to 1-butene, which may be required for productive metathesis. However, it was observed that for catalysts comprising above a certain amount of alumina, 1-butene may begin to react more commonly with itself forming ethylene and 3-hexene. For example, Sample 4 having 5 weight percent alumina was observed to have lesser conversion of 2-butene than Samples 6, 7 and A2.

The results of Table 4 further show that incorporating tungsten into the catalyst after the catalyst support has been formed may also increase the occurrence of single site tungsten oxides and thereby improve performance. As previously discussed in this disclosure, for a metathesis and isomerization catalyst, the silica-alumina of the catalyst support particle may contribute primarily to isomerization, while the metathesis functionality may be primarily provided by the metal oxide, such as $WO_3$. Thus, it may be expected that having a vapor-coated catalyst with less than 5 weight percent alumina in the support would increase the isomerization functionality of the catalyst and improve the yield of propene from metathesis of butene.

Throughout this disclosure ranges are provided for various processing parameters and characteristics of the metathesis and isomerization catalyst, metathesis catalyst, or isomerization catalyst. It will be appreciated that when one or more explicit ranges are provided the individual values and the sub-ranges formed within the range are also intended to be provided as providing an explicit listing of all possible combinations is prohibitive. For example, a provided range of 1-10 also includes the individual values, such as 1, 2, 3, 4.2, and 6.8, as well as all the ranges which may be formed within the provided bounds, such as 1-8, 2-4, 6-9, and 1.3-5.6.

It should be apparent to those skilled in the art that various modifications and variations can be made to the described embodiments without departing from the spirit and scope of the claimed subject matter. Thus it is intended that the specification cover the modifications and variations of the various described embodiments provided such modifications and variations come within the scope of the appended claims and their equivalents.

TABLE 4

Effect of alumina content on metathesis and isomerization.

| | Preparation Method | Tungsten content | Silica content | Alumina content | Conversion 2-butene (mol %) | Propene yield (mol %) |
|---|---|---|---|---|---|---|
| Sample 5 | Aerosol | 10 weight percent | 100 weight percent | 0 weight percent | 55.51% | 14.89% |
| Sample 6 | Aerosol | 10 weight percent | 98 weight percent | 2 weight percent | 67.73% | 18.36% |
| Sample 7 | Aerosol | 2.5 weight percent | 98 weight percent | 2 weight percent | 64.55% | 16.24% |
| Comparative Sample A1 | Wet Impregnation | 2.5 weight percent | 100 weight percent | 0 weight percent | 51.79% | 5.85% |
| Comparative Sample A2 | Wet Impregnation | 10 weight percent | 100 weight percent | 0 weight percent | 60.21% | 11.82% |

What is claimed is:

1. A method for reacting a chemical stream, the method comprising:

contacting the chemical stream with a catalyst to produce a product stream, wherein the chemical stream comprises at least 2-butene and the product stream comprises at least propylene which is the result of both isomerization and metathesis of at least the 2-butene;

wherein the contacting of the chemical stream with the catalyst is at a temperature of less than or equal to 500° C.; and the catalyst comprises:

a plurality of catalyst support particles comprising from 0.1 weight percent to 5 weight percent alumina and from 95 weight percent to 99.9 weight percent silica based on the total weight of the catalyst support particles; and a catalytically active compound deposited onto surfaces of the plurality of catalyst support particles, the surfaces of the plurality of catalyst support particles being accessible to gases and vapors, wherein the catalytically active compound comprises tungsten and the catalytically active compound is deposited on from 1% to 50% of the surfaces of the catalyst support particles that are accessible to gases and vapors.

2. The method of claim 1, wherein the chemical stream comprises at least 5 mol. % 2-butene.

3. The method of claim 2, wherein the product stream comprises at least 10 mol. % propylene.

4. The method of claim 1, wherein the chemical stream has a space velocity of at least 1000/hour.

5. The method of claim 1, wherein the catalyst comprises from 2 weight percent to 11 weight percent of the catalytically active compound based on the total weight of the catalyst.

6. The method of claim 1, wherein the catalytically active compound comprises at least one of single atoms, single molecules, clusters, particles, or combinations of these of the catalytically active compound deposited on the surfaces of the plurality of catalyst support particles.

7. The method of claim 1, wherein an interior of the catalyst support particles is substantially free of the catalytically active compounds.

8. The method of claim 1, wherein the catalytically active compound deposited onto surfaces of the plurality of catalyst support particles has an average crystalline size of less than 2.5 nanometers.

9. A method for reacting a chemical stream, the method comprising:

contacting the chemical stream with a catalyst to produce a product stream, wherein the chemical stream comprises at least 2-butene and the product stream comprises at least propylene which is the result of both isomerization and metathesis of at least the 2-butene;

wherein the contacting of the chemical stream with the catalyst is at a temperature of less than or equal to 500° C.; and the catalyst comprises:

a plurality of catalyst support particles comprising from 0.1 weight percent to 5 weight percent alumina and from 95 weight percent to 99.9 weight percent silica based on the total weight of the catalyst support particles; and a catalytically active compound deposited onto surfaces of the plurality of catalyst support particles, the surfaces of the plurality of catalyst support particles being accessible to gases and vapors, wherein the catalytically active compound comprises tungsten and the catalytically active compound is deposited on from 1% to 50% of the surfaces of the catalyst support particles that are accessible to gases and vapors;

wherein the tungsten is not dispersed throughout the catalyst support particles.

10. The method of claim 9, wherein the chemical stream comprises at least 5 mol. % 2-butene.

11. The method of claim 10, wherein the product stream comprises at least 10 mol. % propylene.

12. The method of claim 9, wherein the chemical stream has a space velocity of at least 1000/hour.

13. The method of claim 9, wherein the catalyst comprises from 2 weight percent to 11 weight percent of the catalytically active compound based on the total weight of the catalyst.

14. The method of claim 9, wherein the catalytically active compound comprises at least one of single atoms, single molecules, clusters, particles, or combinations of these of the catalytically active compound deposited on the surfaces of the plurality of catalyst support particles.

15. The method of claim 9, wherein an interior of the catalyst support particles is substantially free of the catalytically active compounds.

16. The method of claim 9, wherein the catalytically active compound deposited onto surfaces of the plurality of catalyst support particles has an average crystalline size of less than 2.5 nanometers.

* * * * *